(12) United States Patent
Lihme et al.

(10) Patent No.: US 10,457,704 B2
(45) Date of Patent: Oct. 29, 2019

(54) SEPARATION PROCESSES FOR PEA PROTEIN

(71) Applicant: Upfront Chromatography A/S, Copenhagen (DK)

(72) Inventors: Allan Otto Fog Lihme, Farum (DK); Marie Bendix Hansen, Frederiksberg (DK); Martin Pontoppidan, Kgs. Lyngby (DK)

(*) Notice: Subject to any disclaimer, the term of this patent is extended or adjusted under 35 U.S.C. 154(b) by 569 days.

(21) Appl. No.: 15/114,812

(22) PCT Filed: Jan. 29, 2015

(86) PCT No.: PCT/EP2015/051798
§ 371 (c)(1),
(2) Date: Jul. 27, 2016

(87) PCT Pub. No.: WO2015/114045
PCT Pub. Date: Aug. 6, 2015

(65) Prior Publication Data
US 2016/0340385 A1    Nov. 24, 2016

(30) Foreign Application Priority Data

Jan. 29, 2014 (DK) ................................ 2014 70040

(51) Int. Cl.
| | | |
|---|---|---|
| *A61K 36/48* | (2006.01) |
| *C07K 1/22* | (2006.01) |
| *A23J 1/14* | (2006.01) |
| *C07K 14/42* | (2006.01) |
| *A23L 33/185* | (2016.01) |

(52) U.S. Cl.
CPC ..................... *C07K 1/22* (2013.01); *A23J 1/14* (2013.01); *A23L 33/185* (2016.08); *C07K 14/42* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,955,082 A * | 9/1999 | Bodnaryk | ............ | A01N 65/20 424/757 |
| 7,186,807 B2 | 3/2007 | Salome et al. | | |
| 8,124,162 B2 | 2/2012 | Passe et al. | | |
| 2012/0128832 A1 | 5/2012 | Smith | | |

FOREIGN PATENT DOCUMENTS

| | | | |
|---|---|---|---|
| CN | 101029076 A | 9/2007 | |
| CN | 101974593 A | 2/2011 | |
| EP | 1645620 A1 | 4/2006 | |
| EP | 1977653 A1 | 10/2008 | |
| GB | 2494409 A | 3/2013 | |
| WO | 0158924 A2 | 8/2001 | |
| WO | 2002005922 | 1/2002 | |
| WO | 2005121165 A1 | 12/2005 | |
| WO | 2008086811 A1 | 7/2008 | |
| WO | WO-2011050471 A1 * | 5/2011 | ........... C07K 14/415 |
| WO | 2011/082358 A1 | 7/2011 | |
| WO | 2011093693 A1 | 8/2011 | |
| WO | WO-2011122937 A1 * | 10/2011 | ........... A61K 38/011 |
| WO | 2012055986 A1 | 5/2012 | |
| WO | 2014064132 A1 | 5/2014 | |

OTHER PUBLICATIONS

Heppell et al.; A Comparison of the Antigenicity of Soya-bean-based Infant Formulas; British Journal of Nutrition; 1987; pp. 393-403; vol. 58.
Croy et al.; The purification and characterization of a third storage protein (convicilin) from the seeds of pea; Biochem J.; 1980; 191; pp. 509-516.
Geuguen et al.; Large-scale purification and characterisation of pea globulins; J. Sci. Food Agric.; 1984; 35; pp. 1024-1033.
Larré et al.; Comparison between six anion exchangers in medium-pressure liquid chromatography; Journal of Chromatography; 1986; 361; pp. 169-178.
Author Unknown; Patent Cooperation Treaty International-Type Search Report for International Application No. DK2014/70040; dated Sep. 23, 2014.
Author Unknown; Patent Cooperation Treaty International Search Report for International Application No. PCT/EP2015/051798; dated Mar. 25, 2015.

* cited by examiner

Primary Examiner — Russell G Fiebig
(74) Attorney, Agent, or Firm — K&L Gates LLP

(57) ABSTRACT

The invention provides a process for the separation of pea protein. The process begins with an aqueous extract or solution of pea protein, which is passed through at least one expanded bed absorption (EBA) process. The EBA process comprises contacting the aqueous extract or solution of pea protein with at least one adsorbent resin, said adsorbent resin comprising at least one ligand (L1 or L2), having particular chemical structures. Proteins of interest are isolated by eluting them from said adsorbent resin. The invention also provides various protein compositions obtainable via the method of the invention.

7 Claims, 12 Drawing Sheets

US 10,457,704 B2

SEPARATION PROCESSES FOR PEA PROTEIN

FIELD OF THE INVENTION

Figure 1:
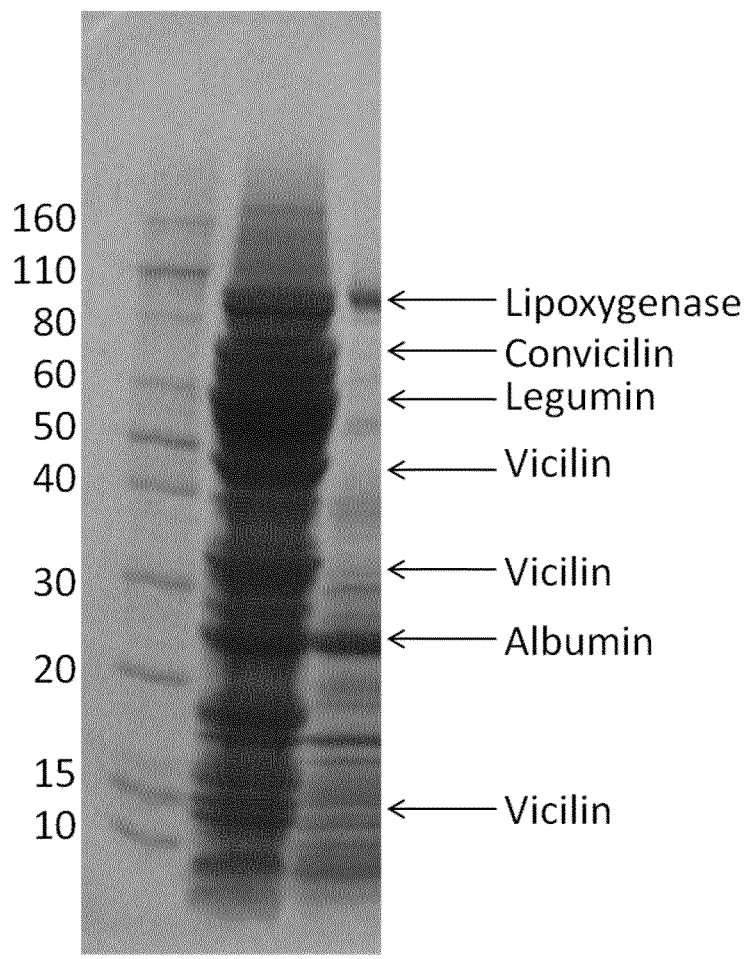

The present invention relates to a separation process for pea protein, as well as purified pea protein obtained from said process.

BACKGROUND OF THE INVENTION

Peas (the seed from the *Pisum Sativum* plant) is an important source of protein for humans and animals, both in its unprocessed and processed form.

WO 2011/122937, WO 1998/033388 and WO 2011/050471 all concern various aspects of isolating, purifying and using pea protein. In addition, Croy et al. Biochem J. 1980, 191, 509-516 discusses the purification and characterisation of convicilin from peas.

Previous processes for isolating pea protein fractions have typically involved precipitation of given fractions. In salt fractionations, legumin precipitates in salt, and vicilin remains soluble. However, convicilin has proved to be a contaminant, and is difficult to avoid when isolating a vicilin-rich fraction. Legumin fractions are also often contaminated with convicilin. Convicilin contamination is typical in large-scale isolation processes (see e.g. Geuguen et al. J. Sci. Food Agric. 1984, 35, 1024-1033; Lame & Gueguen, J. Chromatogr. 1986, 361, 169-178).

OBJECT OF THE INVENTION

Despite the advances made to date, there remains a need for alternative and improved processes for purification and isolation of proteins from aqueous extracts or solutions of pea protein.

SUMMARY OF THE INVENTION

It has been found by the present inventor(s) that certain ligands show selective affinity for the various proteins in pea protein. So, in a first aspect the present invention relates to a process for the separation of pea protein, said process comprising the steps of:
i. providing an aqueous extract of pea protein or a solution of pea protein, said extract or solution of pea protein comprising at least two types of pea proteins;
ii. passing said aqueous extract or solution of pea protein through at least one expanded bed absorption process, wherein said expanded bed absorption process comprises contacting said aqueous extract or solution of pea protein with at least one adsorbent resin which selectively adsorbs at least a first type of pea protein to provide a non-bound protein fraction and a bound protein fraction, said adsorbent resin comprising:
at least one ligand (L1), said at least one ligand (L1) comprising an aromatic or heteroaromatic ring system and one or more acidic groups, or
at least one ligand (L2), said at least one ligand (L2) comprising an alkylamine or alkylarylamine, wherein said alkylamine or alkylarylamine moieties in ligands (L2) comprise an amine substituted with one or more groups selected from:
  a. an aryl, benzyl or heteroaryl group;
  b. an alkyl group having 4-16 carbon atoms which may be straight, branched or cyclic;
  or combinations thereof;
iii. isolating said first type of pea protein from said adsorbent resin, by elution of either the non-bound protein fraction or of the bound protein fraction; and
iv. isolating the second type of pea protein from said adsorbent resin to provide a second pea protein composition which is depleted in said first type of pea protein.

Further details of the method, and the ligands L1 and L2 are given in the following detailed description of the invention, and the appended claims.

The invention also provides pea protein compositions, obtained by the processes of the invention.

LEGENDS TO THE FIGURES

FIGS. 1-11 illustrate SDS-PAGE gels for the examples of the invention.

FIGS. 12-16*b* illustrate properties of the pea proteins isolated according to the invention, in comparison to commercial pea protein sources.

DETAILED DISCLOSURE OF THE INVENTION

As set out above, the invention provides a process for the separation of pea protein, said process comprising the steps of:
i. providing an aqueous extract of pea protein or a solution of pea protein, said extract or solution of pea protein comprising at least two types of pea proteins;
ii. passing said aqueous extract or solution of pea protein through at least one expanded bed absorption process, wherein said expanded bed absorption process comprises contacting said aqueous extract or solution of pea protein with at least one adsorbent resin which selectively adsorbs at least a first type of pea protein to provide a non-bound protein fraction and a bound protein fraction, said adsorbent resin comprising:
at least one ligand (L1), said at least one ligand (L1) comprising an aromatic or heteroaromatic ring system and one or more acidic groups, or
at least one ligand (L2), said at least one ligand (L2) comprising an alkylamine or alkylarylamine, wherein said alkylamine or alkylarylamine moieties in ligands (L2) comprise an amine substituted with one or more groups selected from:
  a. an aryl, benzyl or heteroaryl group;
  b. an alkyl group having 4-16 carbon atoms which may be straight, branched or cyclic;
  or combinations thereof;
iii. isolating said first type of pea protein from said adsorbent resin, by elution of either the non-bound protein fraction or of the bound protein fraction; and
iv. isolating the second type of pea protein from said adsorbent resin to provide a second pea protein composition which is depleted in said first type of pea protein.

Suitably, the steps of the process are carried out sequentially, without intervening steps.

Peas and Pea Protein

The pea is the seed of the *Pisum sativum* plant, is a leguminous crop grown in many parts of the world. Peas are of great economic importance as a source of food and food ingredients.

Pea protein is a general term for the protein present in peas. Peas contain about 25% protein The large protein fractions in peas are:
1. Lectin
2. Legumin (similar to soy glycinin), 60 kDa and can be divide into subunits of 40 kDa and 20 kDa.
3. Vicilin, 50 kDa and can be divide into subunits of 33, 30, 19, 17 and 12.5 kDa.
4. Convicilin, 70 kDa Complex laboratory procedures have been developed to fractionate proteins from each other. Such techniques cannot be practically applied for commercial scale production. Some of these techniques are also difficult to reproduce because small variations in the procedures significantly alter the final composition of the product.

The Process

The process according to the invention begins from a crude aqueous extract of pea protein or solutions of pea proteins. Typically, the aqueous extract of pea protein is obtained by extracting peas or a pea product (e.g. crushed peas or pea flour) with water or a dilute acid or base. Extraction is preferably carried out for between 0.1 and 20 hours, at a temperature of between 1 and 60° C. The water may have a near-neutral pH (pH 6.5-7.5), or may be alkaline, e.g. pH 8.0-pH 12. In some instances the pH of the extraction mixture will be kept constant during extraction within a preferred range by addition of an aqueous base.

In some instances the pea protein will be a solution of pea protein derived from a crude extract by further processing such as precipitation, centrifugation and filtration including membrane filtration such as ultrafiltration, nanofiltration and microfiltration. In a preferred embodiment the pea protein solution is prepared from a protein precipitate obtained by acidification of a near neutral or alkaline pea protein extract.

The pea proteins can come from a "full" extraction of all pea proteins in the peas. Pea proteins can also come from pea whey from which most of the protein has been precipitated at low pH (~pH 4.5) and leaving the low-pH-soluble proteins in the extract.

In order to match the pH of the separation process, the aqueous extract or solution of pea protein may be pH-adjusted prior to step (ii), preferably to a pH in the range 2.0-9.0. Adjusting pH may lead to precipitation of proteins in the aqueous extract, and thus the pH-adjusted pea protein extract may be decanted, centrifuged or filtered to remove non-soluble material prior to step (ii).

The aqueous extract or solution of pea protein comprises at least two types of pea proteins—a first type and a second type.

The aqueous extract or solution of pea protein is passed through at least one separation process, which separation process comprises contacting said aqueous extract of pea protein with at least one adsorbent resin.

The adsorbent resin selectively adsorbs at least a first type of pea protein, and potentially adsorbs further pea protein. A non-bound protein fraction and a bound protein fraction are thus obtained.

The separation process is a solid phase adsorption process: expanded bed absorption (EBA).

Expanded Bed Adsorption (EBA)

Among the various industrial chromatographic separation techniques developed in recent years, Expanded Bed Adsorption (EBA) has been successfully introduced to the certain fields of biotechnology industry. EBA is a type of fluidised bed adsorption wherein the level of back-mixing is kept at a minimum. Compared with other chromatographic separation technologies, EBA offers a significant advantage because it can be used directly with non-clarified feed.

During EBA, the bed of adsorbent resin is allowed to expand inside the chromatographic column when a flow of liquid is applied. Expansion of the bed is often effected in a column having a net structure provided at each of its ends, which covers the cross-sectional area of the column, or some other perforated devices, which will not generate turbulence in the flow. See, for instance, WO-A-9218237 (Amersham Pharmacia Biotech AB, Sweden). The same effect has also been observed in a system utilising a stirred inlet flow WO-A-9200799, (UpFront Chromatography A/S).

In the expanded bed state, the distances between the adsorbent particles of the resin result in a free passage of particulate impurities in the feed stream. By contrast, traditional packed beds work as depth filters that can clog, resulting in increased back-pressure unless the feed is thoroughly clarified. Since no significant pressure builds up in an EBA column, it is possible to apply EBA without the limitations in size and flow rate normally associated with packed-bed columns. Thus, in a preferred embodiment of the present invention the adsorption process does not involve a packed bed.

An EBA process may be characterised by very limited back-mixing of the liquid inside the column as opposed to the well know turbulent fluidised beds. Back-mixing in a bed is often measured as axial dispersion ('vessel dispersion number"), see Levenspiel, "Chemical Reaction Engineering" 2nd Edition, John Wiley & Sons (1972).

The purification may be performed efficiently by applying the aqueous extract of pea protein to the adsorbent column at a linear flow rates of at least 3 cm/min, such as at least 5 cm/min, e.g. at least 8 cm/min, such as at least 10 cm/min e.g. 20 cm/min. Typically the flow rate is selected in the range of 5-50 cm/min, such as in the range of 5-15 cm/min, e.g. in the range of 10-30 cm/min, such as in the range of 25-50 cm/min.

The temperature of the pea protein solution/extract is preferably in the range of 1° C.-90° C. such as in the range of 5° C.-18° C., such as in the range of 7° C.-15° C., such as in the range of 19° C.-80° C., such as in the range of 19° C.-70° C., such as in the range of 25° C.-65° C., such as in the range of 45° C.-60° C.

When the aqueous extract or solution of pea protein is added to the adsorbent column, the ratio between the adsorbent particle present in the column and the material suspension may be optimized in order to retain a high capacity of the adsorbent column and to obtain a high purity of the protein product to be purified. In a preferred embodiment of the present invention the adsorbent present in the column relative to the aqueous extract of pea protein to be loaded on to the column are provided at a ratio of at least 1:0.5, such as at least 1:1, e.g. at least 1:3, such as at least 1:5, e.g. at least 1:8, such as at least 1:10, e.g. at least 1:12, such as at least 1:15, e.g. at least 1:20, such as at least 1:25, e.g. 1:30, such as 1:30 measured on a volume/volume basis.

The first type of pea protein is isolated from said adsorbent resin by elution of either the non-bound protein fraction or of the bound protein fraction.

The separation process may function in a number of ways, which will now be described.

Typically the first type of pea protein fraction remains adsorbed onto the resin as the bound protein fraction, while the second type of pea protein (being the non-bound protein fraction) is eluted in a first elution (washing) step. This is followed by a second elution step which releases the first type of pea protein (being the bound protein fraction).

Alternatively the second type of pea protein remains adsorbed onto the resin while the first type of pea protein is eluted from said adsorbent resin during a first elution (washing) step. In one or more subsequent elution steps the second type of pea protein is then released and isolated essentially free from the first type of pea protein.

In one aspect, essentially the entire pea protein, including the first type of pea protein, is initially adsorbed onto said adsorbent resin, and the first type of pea protein is then eluted from said adsorbent resin in a second elution step (following a first elution (washing) step to remove other non-bound substances) with or without a part of the the first type of pea protein and remaining second type of pea proteins are then eluted in a third or further subsequent elution steps.

In order to obtain the purified first type of pea protein, the elution may be performed by any method conventionally described and known in the prior art. The elution of the adsorbed protein products may be performed with a solution, typically selected from the group consisting of dilute base, dilute acid, dilute buffer, dilute salt solution and water or combinations hereof. In a preferred embodiment the eluting and/or washing step is performed with a dilute solution so as to minimise the amount of salt and other unwanted substances present in the eluted product.

Preferably, the dilute solution used for elution of the first type of pea protein fraction and/or the second type of pea protein products has a salt, buffer, acid or base concentration of less than 200 mM, preferably less than 100 mM, preferably less than 50 mM, preferably less than 30 mM, even more preferably less than 20 mM. The determination of the salt, buffer, acid or base concentration is performed directly on the eluate fraction containing the protein or proteins to be isolated without additional dilution of the eluate fraction. Common, low cost and non-toxic salt, buffers, acids and bases are applicable. Specifically preferred salts are sodium chloride, potassium chloride, calcium chloride, ammonium chloride. Specifically preferred buffers are citrate, lactate, acetate, phosphate, formate and carbonate buffers. Specifically preferred acids are citric acid, phosphoric acid, sulphuric acid, acetic acid, formic acid, hydrochloric acid. Specifically preferred are the bases sodium hydroxide (NaOH), potassium hydroxide (KOH), calcium hydroxide ($Ca(OH)_2$), ammonium hydroxide ($NH_4OH$). All of these may be combined to achieve an optimal elution procedure.

In an embodiment of the present invention elution may be performed using an eluent comprising less than 5% (v/v) of organic solvents, such as less than 3% (v/v) of organic solvent, e.g. less than 1% (v/v) organic solvent, such as 0% (v/v) of organic solvent.

Adsorbent Resin

In an embodiment of the present invention the adsorbent resin comprises at least one ligand (L1). The ligand (L1) comprises an aromatic or heteroaromatic ring system and one or more acidic groups.

Preferably the ligands (L1) comprising an aromatic or heteroaromatic ring-system and/or one or more acidic groups have a molecular weight of at the most 2000 Dalton, such as at the most 1000 Dalton such as at the most 500 Dalton.

The aromatic ring system suitably comprises a phenyl or naphthyl radical.

In an embodiment of the present invention the heteroaromatic moiety may be selected from monocyclic heteroaromatic radicals selected from thiophene, furan, pyran, pyrrole, imidazole, pyrazole, isothiazole, isoxazole, pyridine, pyrazine, pyrimidine, and pyridazine radicals; and bicyclic heteroaromatic radicals selected from indole, purine, quinoline, benzofuran, benzimidazole, benzothiazole, and benzoxazole radicals.

In a further embodiment of the present invention the acidic group is selected from a carboxylic acid group (—COOH), a sulfonic acid group (—$SO_2OH$), sulfinic acid group (—S(O)ON), phosphinic acid group (—PH(O)(OH)), phosphonic acid monoester groups (—P(O)(OH)(OR)), and phosphonic acid group (—$P(O)(OH)_2$), preferably carboxylic acid group (—COOH).

Preferably, the ligands (L1) may be derived from compounds selected from methylene-benzoic acids, hydroxy-benzoic acids, amino-benzoic acids, mercapto-benzoic acids, mercapto-nicotinic acids, mercapto-tetrazole acetic acids such as 2-amino-benzoic acid, 3-amino-benzoic acid, 4-amino-benzoic acid, 2-mercapto-benzoic acid, 3-mercapto.benzoic acid, 4-mercapto-benzoic acid, 5-mercapto-1-tetrazole acetic acid, 4-aminophthalic acid, and 5-aminoisophthalic acid.

Suitably, in ligands (L1), said one or more aromatic or heteroaromatic ring system is substituted by said one or more acidic groups. The ligands L1 may comprise more than one acidic group as well as other substituents such as basic and neutral substituents.

In an alternative embodiment of the present invention the adsorbent resin comprises at least one ligand (L2). Ligand (L2) comprises an alkylamine or alkylarylamine. The alkylamine or alkylarylamine moieties in ligands (L2) comprise an amine substituted with one or more groups selected from:
  i. an aryl, benzyl or heteroaryl group;
  ii. an alkyl group having 4-16 carbon atoms which may be straight, branched or cyclic, such as e.g., butyl, isobutyl, tert-butyl, pentyl, hexyl, heptyl, octyl, nonyl, decyl, undecyl, dodecyl, cyclopentyl, cyclohexyl or decalinyl;
or combinations thereof.

Ligands (L2) may be selected from butylamine, hexylamine, octylamine di-butylamine, pentylamine, n-pentylamine, N,N-di-methyl-1,3-di-aminopropane, 1,3-diaminopropane, 1,6-diamino hexane, 1,6-diamino hexane, 1,8-aminooctane, 1,9-di-aminononane, 1,12-aminododecane, 2-aminobenzylamine, 2-aminobenzimidazole, 2-aminoimidazole, 2,4-diamino-6-hydroxypyrimidine, benzylamine or xylylene diamine.

Particularly preferred ligands (L2) have a C/N ratio (defined as the number of carbon atoms per nitrogen atom in the chemical formula) of at least 4, such as at least 5, such as at least 6.

In an embodiment of the present invention the concentration of the ligands (L1 or L2) is in the range of 10-990 µmol/g dry matter of adsorbent resin.

In yet an embodiment of the present invention the concentration of the ligands (L1 or L2) is in the range of 1-145 µmol/ml of hydrated, sedimented adsorbent resin.

In a further embodiment of the present invention the concentration of the ligands (L1 or L2) is in the range of 1-130 µmol/g wet, but suction-drained adsorbent resin.

Preferably the concentration of the ligands (L1 or L2) is in the range of 10-100 µmol/g wet, but suction-drained, adsorbent resin, such as in the range of 15-80 µmol/g wet, but suction-drained, adsorbent resin, such as in the range of 20-60 µmol/g wet, but suction-drained, adsorbent resin.

Besides the ligand (L1 or L2), the adsorbent resin comprises polymeric base matrix, which constitutes the bulk of the adsorbent resin, and upon which the ligands (L1 or L2) are supported.

The polymeric base matrix may be sought among certain types of natural or synthetic organic polymers, typically selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixtures thereof. A preferred group of polymeric base matrices are polysaccharides, such as agarose.

In an embodiment of the present invention the adsorbent resin is in the form of a particle. The adsorbent resin particle may be at least partly permeable to the protein to be isolated in order to ensure a significant binding capacity in contrast to impermeable particles that can only bind the target protein on its surface, resulting in relatively low binding capacity. The adsorbent resin particle may be of an array of different structures, compositions and shapes.

The adsorbent may further be in the form of a porous fibre or a porous membrane.

The ligands L1 or L2 may be attached to the polymer base matrix by any type of covalent bond known per se to be applicable for this purpose, either by a direct chemical reaction between the ligand and the solid phase material or by a preceding activation of the polymer base matrix or of the ligand with a suitable reagent known per se making it possible to link the matrix and the ligand.

Examples of such suitable activating reagents are epichlorohydrin, epibromohydrin, allyl-glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides, are preferred.

Especially interesting activating reagents are believed to be epoxy-compounds such as epichlorohydrin, allyl-glycidylether and butanedioldiglycidylether. In certain instances the activating reagent may even constitute a part of the functionality contributing to the binding of immunoglobulins to the polymer base matrix. e.g. in cases where divinyl sulfone is used as the activating reagent. In other cases the activating reagent is released from the matrix during reaction of the functional group with the matrix. This is the case when carbodiimidazoles and carbodiimides are used.

The above mentioned possibilities makes it relevant to define the presence of an optional spacer SP1 linking the polymer base matrix and the ligand L1 or L2. In the present context the spacer SP1 is to be considered as the part of the activating reagent which forms the link between the matrix and the ligand. Thus, the spacer SP1 corresponds to the activating reagents and the coupling reactions involved. In some cases, e.g. when using carbodiimides, the activating reagent forms an activated form of the matrix or of the ligand reagent. After coupling no parts of the activating reagent is left between the ligand and the matrix, and, thus, SP1 is simply a single bond.

In other cases the spacer SP1 is an integral part of the functional group effecting the binding characteristics, i.e. the ligand, and this will be especially significant if the spacer SP1 comprises functionally active sites or substituents such as thiols, amines, acidic groups, sulfone groups, nitro groups, hydroxy groups, nitrile groups or other groups able to interact through hydrogen bonding, electrostatic bonding or repulsion, charge transfer or the like.

In still other cases the spacer SP1 may comprise an aromatic or heteroaromatic ring which plays a significant role for the binding characteristics of the solid phase matrix. This would for example be the case if quinones or chloro-triazines where used as activation agents for the polymer base matrix or the ligand L1 or L2.

Preferably, the spacer SP1 is a single bond or a biradical derived from an activating reagent selected from epichlorohydrin, allyl-glycidylether, bis-epoxides such as butanedioldiglycidylether, halogen-substituted aliphatic compounds such as 1,3-dichloropropan-2-ol, aldehydes such as glutaric dialdehyde, divinyl sulfone, quinones, cyanogen bromide, chloro-triazines such as cyanuric chloride, 2-fluoro-1-methylpyridinium toluene-4-sulfonates, maleimides, oxazolones, and hydrazides. Preferably the spacer SP1 is selected from short chain aliphatic biradicals, e.g. of the formula —$CH_2$—$CH(OH)$—$CH_2$— (derived from epichlorohydrin), —$(CH_2)_3$—O—$CH_2$—$CH(OH)$—$CH_2$— (derived from allyl-glycidylether) or —$CH_2$—$CH(OH)$—$CH_2$—O—$(CH_2)_4$—O—$CH_2$—$CH(OH)$—$CH_2$— (derived from butanedioldiglycidylether; or a single bond.

Thus, the adsorbent resin particles may be constituted by a number of chemically derivatised porous materials having the necessary density and binding capacity to operate at the given flow rates.

The density of the adsorbent resin particle may be at least 1.3 g/mL, more preferably at least 1.5 g/mL, still more preferably at least 1.8 g/mL, even more preferably at least 2.0 g/mL, more preferably at least 2.3 g/mL, even more preferably at least 2.5 g/mL, most preferably at least 2.8 g/mL in order to enable a high productivity of the process.

In a preferred embodiment of the present invention the adsorbent resin particle has a mean particle size of at most 500 μm, particularly at most 450 μm, more particularly at most 400 μm, even more particularly at most 350 μm, even more particularly at most 300 μm, even more particularly at most 250 μm such as at most 200 μm.

The adsorbent resin particles may comprise one or more non-porous cores, within the polymeric base matrix. The polymeric base matrix acts as a means for covering and keeping multiple (or a single) core materials together. The adsorbent resin particles may be of the conglomerate type, as described in WO 92/00799, having at least two non-porous cores per particle, surrounded by a porous material. The non-porous cores in conglomerate type adsorbent resin particles are suitably of different types and sizes, e.g. a core particle consisting of two or more high density particles held together by surrounding agarose (polymeric base matrix).

The adsorbent resin particles may also be of the pellicular type having a single non-porous core per particle, surrounded by a porous material e.g. a high density stainless steel bead or a solid glass bead coated with agarose.

The non-porous core(s) constitutes typically of at most 50% of the total volume of the adsorbent resin particle, such as at most 40%, preferably at most 30%. The non-porous core(s) may be incidental distributed within the polymeric base matrix and are not necessarily located in the centre of the adsorbent resin particle.

Examples of suitable non-porous core materials are inorganic compounds, metals, heavy metals, elementary non-metals, metal oxides, non metal oxides, metal salts and metal alloys, etc. Examples of such core materials are metal silicates metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred non-porous core materials are tungsten carbamide, tungsten, steel and titanium beads such as stainless steel beads.

Protein Compositions and their Production

The present invention provides routes to pea protein compositions and combined pea protein products.

A second pea protein composition depleted in the first type of pea protein is provided by isolating the second type of pea protein from the adsorbent resin. In the context of the present invention, is the second pea protein is "depleted" in the first type of pea protein, this means that the amount of first pea protein in the second pea protein is reduced by means of the method. However, in one aspect, the first type of pea protein may be completely removed from the second pea protein.

Preferably the first and second type of pea protein is separated so that the first type of pea protein contains less than 30%, such as less than 25%, such as less than 20%, such as less than 15%, such as less than 10%, such as less than 5% of the initial amount of the second type of protein when measured on a weight to weight of the proteins basis before and after the separation process.

Also preferred is that the first and second type of pea protein is separated so that the second type of pea protein contains less than 30%, such as less than 25%, such as less than 20%, such as less than 15%, such as less than 10%, such as less than 5% of the initial amount of the first type of protein when measured on a weight to weight of the proteins basis before and after the separation process.

In some instances both the first and second type of pea proteins will preferably be separated to achieve the above mentioned preferred separation levels for both type of proteins.

The second pea protein composition, depleted in the first type of pea protein, may be denatured to provide a denatured second pea protein composition. Selectivity in the denaturing process can be obtained. Denaturing the second pea protein composition suitably takes place by heating to a temperature between 50° C.-100° C., such as between 50° C.-90° C., such as between 50° C.-80° C., such as between 55° C.-80° C., such as between 60° C.-80° C. Alternatively—or in combination with a heat treatment—enzymatic proteolysis may be applied to inactivate any unwanted proteins such as lipoxygenase, agglutinin and allergenic antigens.

The invention thus relates to a second pea protein composition, obtained by the process described herein.

Health Drink

The isolation of pea protein fractions according to the process of the present invention allows the manufacture of useful food products which can provide beneficial effects. One such useful food product is a health drink comprising pea protein fractions. Suitably, such a health drink has a pH below 7, and could for instance be a fruit juice or a soda.

EMBODIMENTS OF THE INVENTION

1. Embodiment 1

A process for the separation of pea protein, said process comprising the steps of:
  i. providing an aqueous extract of pea protein or a solution of pea protein, said extract or solution of pea protein comprising at least two types of pea proteins;
  ii. passing said aqueous extract or solution of pea protein through at least one expanded bed absorption process, wherein said expanded bed absorption process comprises contacting said aqueous extract or solution of pea protein with at least one adsorbent resin which selectively adsorbs at least a first type of pea protein to provide a non-bound protein fraction and a bound protein fraction, said adsorbent resin comprising:
    at least one ligand (L1), said at least one ligand (L1) comprising an aromatic or heteroaromatic ring system and one or more acidic groups, or
    at least one ligand (L2), said at least one ligand (L2) comprising an alkylamine or alkylarylamine, wherein said alkylamine or alkylarylamine moieties in ligands (L2) comprise an amine substituted with one or more groups selected from:
      c. an aryl, benzyl or heteroaryl group;
      d. an alkyl group having 4-16 carbon atoms which may be straight, branched or cyclic;
    or combinations thereof;
  iii. isolating said first type of pea protein from said adsorbent resin, by elution of either the non-bound protein fraction or of the bound protein fraction; and
  iv. isolating the second type of pea protein from said adsorbent resin to provide a second pea protein composition which is depleted in said first type of pea protein.

Embodiment 2

The process according to any one of the preceding embodiments, wherein the second type of pea protein remains adsorbed onto said resin while said first type of pea protein is eluted from said adsorbent resin.

Embodiment 3

The process according to any one of the preceding embodiments, wherein first and second types of pea protein are initially both adsorbed onto said adsorbent resin, and said first type of pea protein is then eluted from said adsorbent resin.

Embodiment 4

The process according to embodiment 3, wherein eluting said first type of pea protein from said adsorbent resin occurs via an increase in pH of the eluent.

Embodiment 5

The process according to any one of the preceding embodiments, further comprising the step of denaturing the second pea protein composition to provide a denatured second pea protein composition.

Embodiment 6

The process according to embodiment 5, wherein denaturing the second pea protein composition takes place by heating to a temperature between 50° C.-100° C.

Embodiment 7

The process according to any one of the preceding embodiments, wherein the ligands (L1) comprising an aromatic or heteroaromatic ring-system and/or one or more acidic groups have a molecular weight of at the most 2000 Dalton, such as at the most 1000 Dalton such as at the most 500 Dalton.

Embodiment 8

The process according to any one of the preceding embodiments, wherein the ligands (L1) comprise an aromatic ring system, preferably a phenyl or naphthyl radical.

Embodiment 9

The process according to any one of the preceding embodiments, wherein the ligands (L1) comprise a heteroaromatic ring system, which may be selected from monocyclic hetero-aromatic radicals selected from thiophene, furan, pyran, pyrrole, imidazole, pyrazole, isothiazole, isoxazole, pyridine, pyrazine, pyrimidine, and pyridazine radicals; and bicyclic heteroaromatic radicals selected from indole, purine, quinoline, benzofuran, benzimidazole, benzothiazole, and benzoxazole radicals.

Embodiment 10

The process according to any one of the preceding embodiments, wherein the ligands (L1) comprise an acidic group selected from a carboxylic acid group (—COOH), a sulfonic acid group (—$SO_2OH$), sulfinic acid group (—S(O)OH), phosphinic acid group (—PH(O)(OH)), phosphonic acid monoester groups (—P(O)(OH)(OR)), and phosphonic acid group (—P(O)(OH)$_2$), preferably carboxylic acid group (—COOH).

Embodiment 11

The process according to any one of the preceding embodiments, wherein the ligands (L1) are selected from methylene-benzoic acids, hydroxy-benzoic acids, amino-benzoic acids, mercapto-benzoic acids, mercapto-nicotinic acids, mercapto-tetrazole acetic acids such as 2-amino-benzoic acid, 3-amino-benzoic acid, 4-amino-benzoic acid, 2-mercapto-benzoic acid, 3-mercapto.benzoic acid, 4-mercapto-benzoic acid, 5-mercapto-1-tetrazole acetic acid, 4-aminophthalic acid, and 5-aminoisophthalic acid.

Embodiment 12

The process according to any one of the preceding embodiments, wherein—in the ligands (L1)—said one or more aromatic or heteroaromatic ring system is substituted by said one or more acidic groups.

Embodiment 13

The process according to any one of embodiments 1-12, wherein said alkylamine or alkylarylamine moieties in ligands (L2) comprise an amine substituted with one or more groups selected from: an alkyl group having 4-16 carbon atoms which may be straight, branched or cyclic, such as e.g. butyl, isobutyl, tert-butyl, pentyl, hexyl, heptyl, octyl, nonyl, decyl, undecyl, dodecyl, cyclopentyl, cyclohexyl or decalinyl;

Embodiment 14

The process according to embodiment 13, wherein said ligands (L2) are selected from butylamine, hexylamine, octylamine di-butylamine, pentylamine, n-pentylamine, N,N-di-methyl-1,3-di-aminopropane, 1,3-diaminopropane, 1,6-diamino hexane, 1,6-diamino hexane, 1,8-aminooctane, 1,9-di-aminononane, 1,12-aminododecane, 2-aminobenzylamine, 2-aminobenzimidazole, 2-aminoimidazole, 2,4-di-amino-6-hydroxypyrimidine or benzylamine.

Embodiment 15

The process according to any one of the preceding embodiments, wherein the adsorbent resin comprises polymeric base matrix upon which the ligands (L1 or L2) are supported.

Embodiment 16

The process according to any one of the preceding embodiments, wherein the polymeric base matrix is a natural or synthetic organic polymer, selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixtures thereof.

Embodiment 17

The process according to any one of the preceding embodiments, wherein the adsorbent resin is in the form of a particle.

Embodiment 18

The process according to any one of the preceding embodiments, wherein the aqueous extract of pea protein is obtained by extracting peas or a pea product with water at pH 6.5-7.5.

Embodiment 19

The process according to any one of the preceding embodiments, wherein the aqueous extract of pea protein is obtained by extracting peas or a pea product with water at circa pH 9.0.

Embodiment 20

The process according to any one of the preceding embodiments, wherein the aqueous extract of pea protein is pH-adjusted prior to step (ii), preferably to a pH in the range 2.0-9.0.

Embodiment 21

The process according to embodiment 20, wherein the pH-adjusted pea protein extract is centrifuged or filtered to remove non-soluble material prior to step (ii).

Embodiment 22

A second pea protein composition, depleted in said first type of pea protein, obtained by the process of embodiment 1.

Embodiment 23

A denatured second pea protein composition, obtained by the process of embodiment 5.

EXAMPLES

Example 1

1A) Activation of Agarose Beads:

Samples of various high density agarose beads (produced by Upfront Chromatography A/S with an agarose concentration in the range of 3-8% and containing 10% tungsten carbide as a high density filler) having a bead size of 20-350 μm were cross-linked and activated with epichlorhydrin (Aldrich cat. no.: E1055). The resulting concentrations of epoxy groups was determined to vary in the range of 20-100 mmol/L of beads.

1B) Coupling of Ligands to Activated Beads:

The following general procedure was used for coupling ligands to the activated beads described in example 1A.

1) 50 ml of the epoxy-activated beads was washed on a suction filter with 200 ml of deionized water and drained. The drained adsorbent was transferred to a 250 ml plastic bottle 2) The ligand (2.5 g) was dissolved or suspended in 50 ml of deionized water and pH was adjusted to 10.5-12.5 with 2 M NaOH to achieve a fully solubilized ligand solution.

3) The ligand solution was incubated with the drained adsorbent on a roller mixer for 18 hours at room temperature.

4) The adsorbent was washed with five liters of deionized water

For ligands which were poorly-soluble in water the ligand was dissolved or suspended in 50% ethanol and pH adjusted to 10.5-12.5 with 2 M NaOH. After incubation of the ligand solution with the suction-drained adsorbent, the adsorbent was washed with one liter of 50% ethanol followed by four liters of deionized water.

The ligand concentration was determined by acid-base titration of the characteristic functional groups on the coupled ligand.

The following chemical compounds were coupled to epichlorhydrin-activated agarose beads as described in the general procedure above:

4-aminobenzoic acid, 4-mercaptobenzoic acid, 4-aminosalicylic acid, butylamine, hexylamine, octylamine, benzylamine, di-aminopropane, 1.6-diamino hexane (4 and 6% agarose), di-aminooctane, 1,9-di-aminononane, di-aminododecane, 2-aminobenzylamine, neopentylamine, di-butylamine, pentylamine, N,N-di-methyl-di-aminopropane, 2-aminobenzimidazole, 2,4-di-amino-6-hydroxypyrimidine, 2-aminobenzimidazole, 2-aminoimidazole.

1C) Coupling of the Ligand Chloromethylbenzoic Acid to Activated Beads Described in Example 1A 1) 200 ml of the epoxy-activated beads was washed on a suction filter with 800 ml of deionized water and drained. The drained adsorbent was transferred to a 500 ml plastic beaker.

2) 224 ml of deionized water was added. The solution was mixed with a mechanical mixer.

3) 32.5% sodium hydroxide was added to reach a pH of 13.5 (initially 25 ml)

4) 6.7 g of chloromethylbenzoic acid was added.

5) pH was checked every 15 min and 32.5% NaOH was added to keep the pH at 13.5.

6) Every hour 6.7 g of chloromethylbenzoic acid was added.

7) After 8 hours of mixing the adsorbent was washed with five liters of deionized water The ligand concentration was determined by acid-base titration of the characteristic functional groups on the coupled ligand.

1D) Coupling of the Ligand 2-Diethylamino-ethylchloride (DEAE) to Activated Beads Described in EXAMPLE 1A 1) 200 ml of the epoxy-activated beads was washed on a suction filter with 800 ml of deionized water and drained. It was then washed with 600 ml of a 85% N-methylpyrrolidone solution. The drained adsorbent was transferred to a 1000 ml plastic beaker.

2) 200 ml of 85% N-methylpyrrolidone solution was added. The solution was mixed with a mechanical mixer.

3) 12 g of DEAE was added to the solution 4) 50.8 g NaOH was added to the solution 5) After 2 hours the adsorbent was washed with five liters of deionized water The ligand concentration was determined by acid-base titration of the characteristic functional groups on the coupled ligand.

1E) Coupling of the Ligand Sodium Sulphite and Butane Sultone (SP) to Activated Beads Described in EXAMPLE 1A 1) 200 ml of the epoxy-activated beads was washed on a suction filter with 800 ml of deionized water and drained. The drained adsorbent was transferred to a 1000 ml plastic bottle.

2) 200 ml of 1.2M sodium sulphite solution was added. The solution was mixed with a mechanical mixer.

3) The ligand solution was incubated with the drained adsorbent on a roller mixer for 18 hours at room temperature.

4) The adsorbent was washed with five liters of deionized water and drained. The drained adsorbent was transferred to a 1000 ml plastic beaker.

3) 100 ml of 35% NaOH was added to the beaker. The beaker with adsorbent and NaOH was placed in a waterbath and heated to 63 degrees Celsius.

4) 4 g SDS was added to the solution.

6) 8 ml of butane sultone was added to the solution every 30 minutes.

5) After 5 hours the adsorbent was washed with five liters of deionized water.

The ligand concentration was determined by acid-base titration of the characteristic functional groups on the coupled ligand.

Example 2

The example describes the production of the pea extract that was used for the following examples.

Dried yellow peas (Cat. No.: 3032 from Unifood Import A/S, Denmark) were milled to create pea flour.

Six extraction methods were used in the flour/water ratio of 1+7:
1. Extraction at near neutral pH
2. Extraction at pH 8.0
3. Extraction at pH 10.0
4. Extraction at pH 8.0 with 0.1M NaCl
5. Extraction at pH 8.0 with 0.5M NaCl
6. Extraction at pH 8.0 with 1.0M NaCl Extraction of Near Neutral pH 250 g of pea flour was mixed with 1750 ml of deionized water. The suspension was mixed for one hour after which the non-soluble fraction was removed by sieving the extract on a 100 μm nylon filter net. The resulting extract was an unclear, milky liquid with a pH of 6.3 and a conductivity of 2.4 mS/cm.

Extraction at pH 8.0

250 g of pea flour was mixed with 1750 ml of deionized water. The suspension was mixed for 1 hour, while during mixing the pH was continuously adjusted to pH 8.0 by the addition of 1 M NaOH. The pH was hereby kept at pH 8.0 during the entire extraction period. Following extraction the non-soluble fraction was removed by sieving the extract on a 100 μm nylon filter net. The resulting extract was an unclear, milky liquid with a pH of 8.0 and a conductivity of 2.6 mS/cm.

Extraction at pH 10.0

250 g of pea flour was mixed with 1750 ml of deionized water. The suspension was mixed for 1 hour, while during mixing the pH was continuously adjusted to pH 10.0 by the addition of 1 M NaOH. The pH was hereby kept at pH 10.0 during the entire extraction period. Following extraction the non-soluble fraction was removed by sieving the extract on a 100 μm nylon filter net. The resulting extract was an unclear, milky liquid with a pH of 10.0 and a conductivity of 3.9 mS/cm.

Extraction at pH 8.0 with 0.1M NaCl 250 g of pea flour was mixed with 1750 ml of 0.1M NaCl solution. The suspension was mixed for 1 hour, while during mixing the pH was continuously adjusted to pH 8.0 by the addition of 1 M NaOH. The pH was hereby kept at pH 8.0 during the entire extraction period. Following extraction the non-soluble fraction was removed by sieving the extract on a 100 μm nylon filter net.

Extraction at pH 8.0 with 0.5M NaCl 250 g of pea flour was mixed with 1750 ml of 0.5M NaCl solution. The suspension was mixed for 1 hour, while during mixing the pH was continuously adjusted to pH 8.0 by the addition of 1 M NaOH. The pH was hereby kept at pH 8.0 during the entire extraction period. Following extraction the non-soluble fraction was removed by sieving the extract on a 100 μm nylon filter net.

Extraction at pH 8.0 with 1.0M NaCl 250 g of pea flour was mixed with 1750 ml of 1.0M NaCl solution. The suspension was mixed for 1 hour, while during mixing the pH was continuously adjusted to pH 8.0 by the addition of 1 M NaOH. The pH was hereby kept at pH 8.0 during the entire extraction period. Following extraction the non-soluble fraction was removed by sieving the extract on a 100 μm nylon filter net.

For the experiments performed as packed bed chromatography, the extracts were centrifuged at 10,000 rpm to remove precipitated and non-soluble material.

Example 3

SDS Page and Dry Matter Analytical Procedures

The performance of each of the tested adsorbents described in the following examples was determined by SDS-PAGE gel electrophoresis according to the following general procedure.

25 μL of pea protein sample (centrifuged at 10.000 RPM to remove particles of insoluble material) was mixed with 25 μL tris-glycine sample buffer (LC2676, Novex by Life Technologies, USA). The resulting solution was boiled in water for 5 min under non-reducing conditions. 20 μL of the boiled sample was loaded on to a precast SDS-PAGE gel cassette (4-20% tris-glycine gradient gel (1 mm), EC6025, Novex by Life Technologies, USA). The gel was running for 1 hour at 200 V, 400 mA. The gel was stained with Coomassie blue dye reagent over night (SimplyBlue™ SafeStain, LC6060).

FIG. 1 shows a SDS-PAGE gel of the pea extract at pH 10.0, pH 8.0 and pH 6.3. A standard molecular marker from Invitrogen (Novex unstained protein standard, LC5801) has been added in order to identify the different proteins. Arrows are present to indicate the identified protein bands.

In the following examples where it is concluded if e.g. the pea lectin, the pea legumin or other specific proteins are binding/not binding to a specific adsorbent, it is based on this SDS-PAGE gel showing the standard marker compared to the specific protein bands appearing on the gel.

FIG. 1 to EXAMPLE 3
Lane 1=Standard marker in kDa
Lane 2=Pea extract pH 6.3

Figure 2:
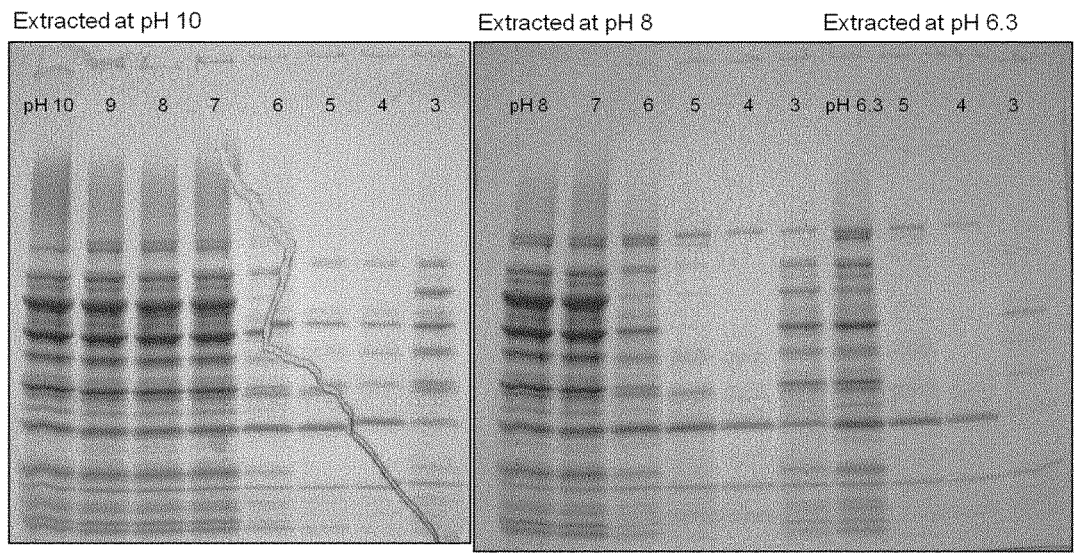

FIG. 2 shows a SDS-PAGE gel of the pea extract at pH 10.0, pH 8.0 and pH 6.3 which have been pH adjusted stepwise to pH 3.0.

FIG. 2 to EXAMPLE 3
Lane 1=Pea extract pH 10.0
Lane 2=Pea extract pH 10.0 then adjusted to pH 9
Lane 3=Pea extract pH 10.0 then adjusted to pH 8
Lane 4=Pea extract pH 10.0 then adjusted to pH 7
Lane 5=Pea extract pH 10.0 then adjusted to pH 6
Lane 6=Pea extract pH 10.0 then adjusted to pH 5
Lane 7=Pea extract pH 10.0 then adjusted to pH 4
Lane 8=Pea extract pH 10.0 then adjusted to pH 3
Lane 9=Pea extracted pH 8.0
Lane 10=Pea extracted pH 8.0 then adjusted to pH 7
Lane 11=Pea extracted pH 8.0 then adjusted to pH 6

Lane 12=Pea extracted pH 8.0 then adjusted to pH 5
Lane 13=Pea extracted pH 8.0 then adjusted to pH 4
Lane 14=Pea extracted pH 8.0 then adjusted to pH 3
Lane 15=Pea extracted pH 6.3
Lane 16=Pea extracted pH 6.3 then adjusted to pH 5
Lane 17=Pea extracted pH 6.3 then adjusted to pH 4
Lane 18=Pea extracted pH 6.3 then adjusted to pH 3

Figure 3:
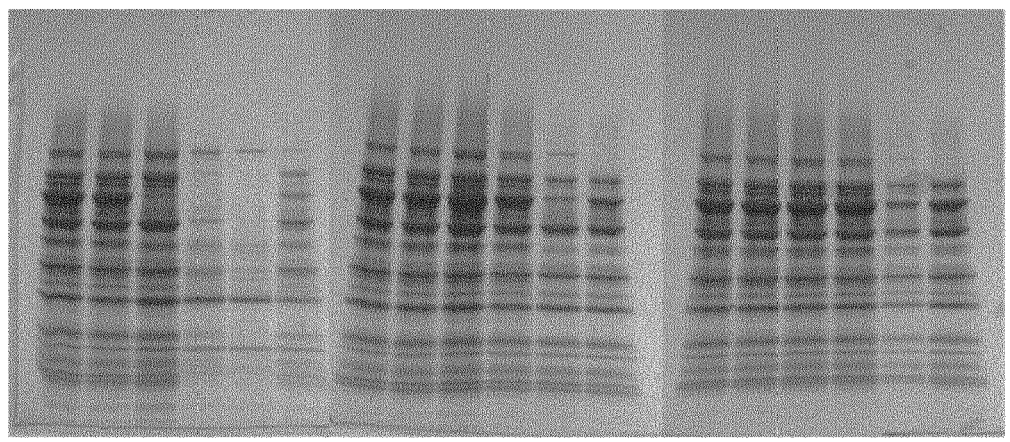

FIG. 3 shows SDS-PAGE gels of the pea extract at pH 8.0 with 0.1, 0.5, and 1.0M NaCl.

Lane 1=Pea extracted at pH 8.0 with 0.1M NaCl
Lane 2=Pea extracted at pH 8.0 with 0.1M NaCl then adjusted to pH 7
Lane 3=Pea extracted at pH 8.0 with 0.1M NaCl then adjusted to pH 6
Lane 4=Pea extracted at pH 8.0 with 0.1M NaCl then adjusted to pH 5
Lane 5=Pea extracted at pH 8.0 with 0.1M NaCl then adjusted to pH 4
Lane 6=Pea extracted at pH 8.0 with 0.1M NaCl then adjusted to pH 3
Lane 7=Pea extracted at pH 8.0 with 0.5M NaCl
Lane 8=Pea extracted at pH 8.0 with 0.5M NaCl then adjusted to pH 7
Lane 9=Pea extracted at pH 8.0 with 0.5M NaCl then adjusted to pH 6
Lane 10=Pea extracted at pH 8.0 with 0.5M NaCl then adjusted to pH 5
Lane 11=Pea extracted at pH 8.0 with 0.5M NaCl then adjusted to pH 4
Lane 12=Pea extracted at pH 8.0 with 0.5M NaCl then adjusted to pH 3
Lane 13=Pea extracted at pH 8.0 with 1.0M NaCl
Lane 14=Pea extracted at pH 8.0 with 1.0M NaCl then adjusted to pH 7
Lane 15=Pea extracted at pH 8.0 with 1.0M NaCl then adjusted to pH 6
Lane 16=Pea extracted at pH 8.0 with 1.0M NaCl then adjusted to pH 5
Lane 17=Pea extracted at pH 8.0 with 1.0M NaCl then adjusted to pH 4
Lane 18=Pea extracted at pH 8.0 with 1.0M NaCl then adjusted to pH 3

Dry Matter Determination

The amount of non-dialyzable dry matter recovered in the protein eluate of selected examples was determined according to the following general procedure:

A fixed amount of eluate (7.5 ml) was dialyzed for 18 hours against water to eliminate small molecules such as salts and buffer substances from the protein sample (dialysis membrane: Spectra/Por molecular porous membrane tubing a cut off of 6-8 kD, Spectrum Laboratories, USA). Following dialysis the dialyzed protein solution was transferred to a foil beaker and dried over night (24 hours) at 100° C. The amount of dry matter (protein) was calculated as the weight of the beaker after drying minus the weight of the beaker. Quantitative amino acid analysis generally confirmed that more than 90% of the dry matter was indeed protein related.

Example 4

Adsorbents produced according to EXAMPLE 1 were tested for the ability to bind pea proteins at pH 4.5, 6.3, and 8.0. The following ligands were tested:

4-mercaptobenzoic acid at pH 4.5, benzylamine at pH 6.3, hexylamine at pH 6.3 and Q-reagents at pH 8.0.

Procedure 1 ml of adsorbent was transferred and packed into a small open-top plastic column (Poly-Prep Chromatography Column cat. No.: 731-1550 Biorad, USA) to form a packed bed of approx. 20 mm bed height. The flow rate applied through the packed was approx. 0.5 ml/min for all tests. After packing the adsorbent was equilibrated with 10 ml 10 mM sodium citrate pH 4.5, or 100 mM $K_2HPO_4$ pH 6.0, or 100 mM $K_2HPO_4$ pH 8.0 depending on extract pH. The pea extract (produced at near neutral pH according to EXAMPLE 2 but in the ratio of 1+2) was pH-adjusted with 1 M HCl to pH 6.0 and 4.5 and pH-adjusted with 1 M NaOH to pH 8.0. All extracts were centrifuged at 6,000 RPM to remove precipitated and non-soluble material. 10 ml of the centrifuged extract was loaded onto the column. The flow through (non-bound proteins) was collected in two fractions. The column was then washed with 5 ml of 10 mM sodium citrate pH 4.5, or 100 mM $K_2HPO_4$ pH 6.0, or 100 mM $K_2HPO_4$ pH 8.0 depending on extract pH. The flow through (non-bound and loosely bound proteins) was collected in one 5 ml fraction. The bound proteins were subsequently released from the column (eluted) by applying 10 ml 50 mM NaOH or 1M NaCl for the anion exchangers. The flow through (eluted proteins, eluate) was collected in one 10 ml fraction. The performance of the adsorbent was determined by SDS-PAGE (as described in EXAMPLE 3). See FIG. 4.

The results indicate that the tested aromatic acid ligand binds different proteins than the other tested ligands. The 4-mercaptobenzoic acid ligand, see lane 5 representing the eluate fraction containing bound proteins, is binding lipoxygenase at approx. 100 kDa and albumin at approx. 20-25 kDa. The significant band of vicilin is left in the flow through (see lanes 2 and 3). For the benzylamine, hexylamine, and Q-reagents the binding patterns are similar (see lanes 10, 15, and 20). They all bind significant amounts of convicilin (70 kDa) and legumin (60 kDa) but the larger subunits of vicilin at 50 and 33 kDa is left in the flow through (see lanes 7, 8, 11, 12, 16, and 17).

Figure 4:
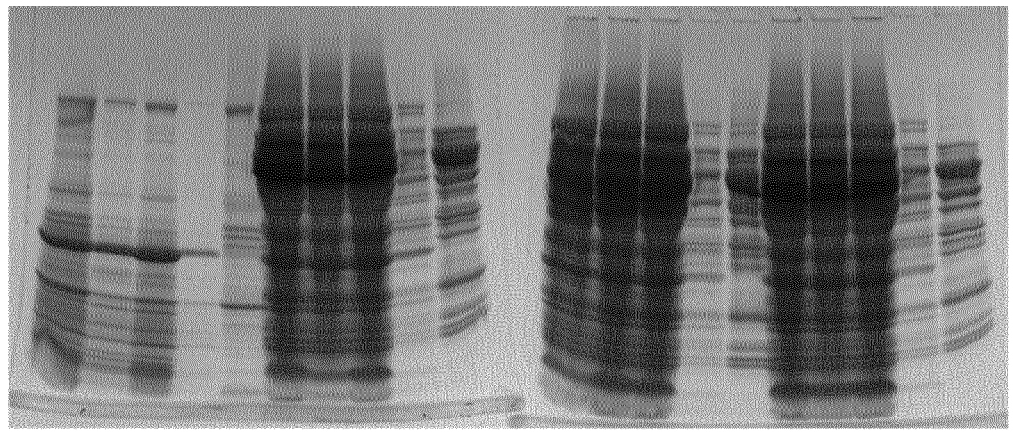
Figure 5:
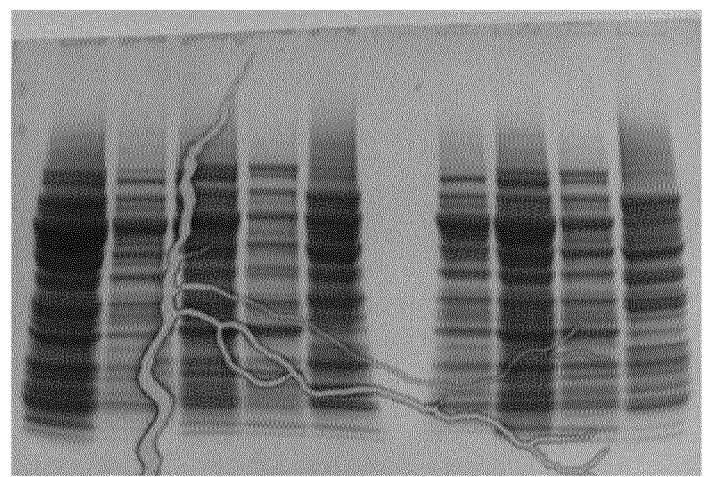
Figure 6:
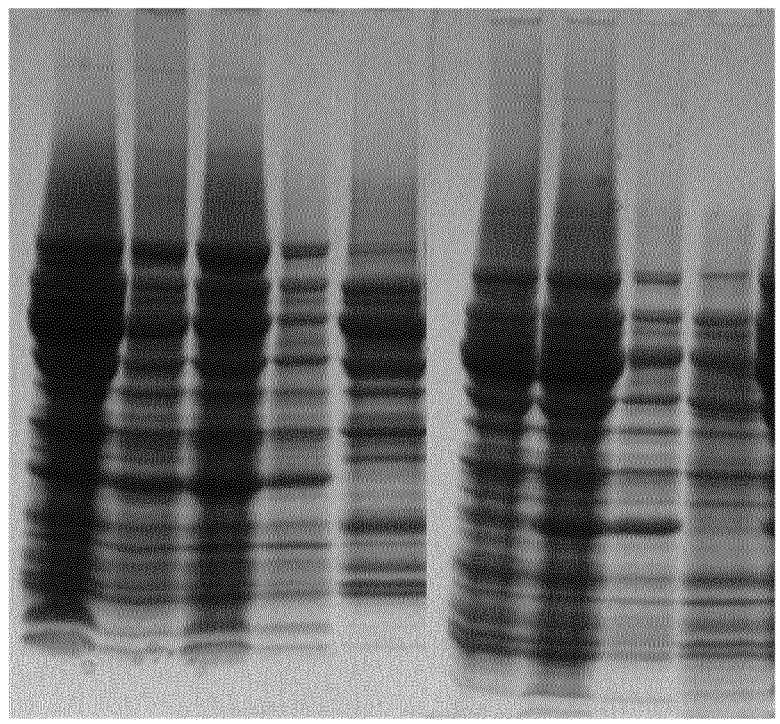

FIG. 4 for EXAMPLE 4

Lane 1=Pea extract at pH 4.5
Lane 2=Flow through fraction 1 (non-bound proteins) from load of adsorbent with the ligand 4-mercaptobenzoic acid
Lane 3=Flow through fraction 2 (non-bound proteins) from load of adsorbent with the ligand 4-mercaptobenzoic acid
Lane 4=Wash fraction (non-bound proteins) from load of adsorbent with the ligand 4-mercaptobenzoic acid
Lane 5=Eluate (Bound and subsequently released proteins) from adsorbent with the ligand 4-mercaptobenzoic acid
Lane 6=Pea extract at pH 6.3
Lane 7=Flow through fraction 1 (non-bound proteins) from load of adsorbent with the ligand benzylamine
Lane 8=Flow through fraction 2 (non-bound proteins) from load of adsorbent with the ligand benzylamine
Lane 9=Wash fraction (non-bound proteins) from load of adsorbent with the ligand benzylamine
Lane 10=Eluate (Bound and subsequently released proteins) from adsorbent with the ligand benzylamine
Lane 11=Flow through fraction 1 (non-bound proteins) from load of adsorbent with the ligand hexylamine
Lane 12=Flow through fraction 2 (non-bound proteins) from load of adsorbent with the ligand hexylamine
Lane 13=Pea extract at pH 6.3
Lane 14=Wash fraction (non-bound proteins) from load of adsorbent with the ligand hexylamine Lane 15=Eluate (Bound and subsequently released proteins) from adsorbent with the ligand hexylamine Lane 16=Flow through fraction 1 (non-bound proteins) from load of adsorbent with the ligand Q-reagents Lane 17=Flow through fraction 2 (non-bound proteins) from load of adsorbent with the ligand Q-reagents Lane 18=Pea extract at pH 8.0

Lane 19=Wash fraction (non-bound proteins) from load of adsorbent with the ligand Q-reagents Lane 20=Eluate (Bound and subsequently released proteins) from adsorbent with the ligand Q-reagents Example 5

Adsorbents produced according to EXAMPLE 1 were tested for the ability to bind pea proteins at pH 6.3. The following ligands were tested:

4-mercaptobenzoic acid and benzylamine.

Procedure

Column preparation and flow rate as per Example 4. After packing the adsorbent was equilibrated with 10 ml 10 mM sodium citrate pH 6.0. The pea extract was produced at near neutral pH according to Example 4. The extract was centrifuged at 18,000 RPM to remove non-soluble and precipitated material. 2 ml of the centrifuged extract was loaded onto the column. The flow through (non-bound proteins) was collected in two 1 ml fractions. The adsorbent was washed with 5 ml of 10 mM sodium citrate pH 6.0. The flow through (non-bound and loosely bound proteins) was collected in one 5 ml fraction. The bound proteins were subsequently released from the column (eluted) by applying 10 ml 50 mM NaOH. The flow through (eluted proteins, eluate) was collected in one 10 ml fraction and pH in the eluate fraction was immediately adjusted to pH 7.0 by addition of 1 M HCl.

The performance of the adsorbent was determined by SDS-PAGE (as described in EXAMPLE 3). See FIG. 5.

The results indicate that the benzylamine ligand, see lane 5 representing the eluate fraction containing bound proteins, is binding essentially all the proteins applied to the column but not the lipoxygenase at 100 kDa and the albumin at 20-25 kDa which are left in the flow through and wash fractions, see lanes 2, 3, and 4. For the 4-mercaptobenzoic acid the binding is similar (see lane 10) but the large band of legumin (60 kDa) is not bound. Meaning that legumin at both 60 kDa and albumin 20-25 kDa is not bound. Also here are the lipoxygenase at 100 kDa absent.

FIG. 5, Example 5

Lane 1=Pea extract at pH 6.3

Lane 2=Flow through fraction 1 (non-bound proteins) from load of adsorbent with the ligand benzylamine Lane 3=Flow through fraction 2 (non-bound proteins) from load of adsorbent with the ligand benzylamine Lane 4=Wash (non-bound and loosely bound proteins) of the adsorbent with the ligand benzylamine Lane 5=Eluate (Bound and subsequently released proteins) from adsorbent with the ligand benzylamine Lane 6=Blank Lane 7=Flow through fraction 1 (non-bound proteins) from load of adsorbent with the ligand 4-mercaptobenzoic acid Lane 8=Flow through fraction 2 (non-bound proteins) from load of adsorbent with the ligand 4-mercaptobenzoic acid Lane 9=Wash (non-bound and loosely bound proteins) of the adsorbent with the ligand 4-mercaptobenzoic acid Lane 10=Eluate (Bound and subsequently released proteins) from adsorbent with the ligand 4-mercaptobenzoic acid Example 6

Adsorbents produced according to EXAMPLE 1 were tested for the ability to bind pea proteins at pH 8.0. The following ligands were tested:

DEAE and octylamine.

Procedure

Column preparation and flow rate as per Example 4. After packing the adsorbent was equilibrated with 10 ml 10 mM $K_2HPO_4$ pH 8.0. The pea extract was produced at pH 8.0 according to Example 2. The extract was centrifuged at 6,000 RPM to remove non-soluble and precipitated material. 5 ml of the centrifuged extract was loaded onto the column. The flow through (non-bound proteins) was collected in two fractions. The adsorbent was washed with 5 ml of deionized water. The flow through (non-bound and loosely bound proteins) was collected in one 5 ml fraction. The bound proteins were subsequently released from the column (eluted) by applying 10 ml 1M NaCl for the DEAE and 10 ml 100 mM phosphoric acid pH 2.3 for the octylamine. The flow through (eluted proteins, eluate) was collected in one 10 ml fraction and pH in the eluate fraction was immediately adjusted to pH 7.0.

The performance of the adsorbent was determined by SDS-PAGE (as described in EXAMPLE 3). See FIG. 6.

The results indicate that both ligands have similar binding patterns, see lanes 5 and 9 representing the eluate fraction containing bound proteins although the ligand DEAE binds more than the ligand octylamine. They bind essentially all the proteins applied to the column but not the lipoxygenase at 100 kDa and the albumin at 20-25 kDa which are left in the flow through and wash fractions, see lanes 2, 3, 4, 6, 7, and 8.

FIG. 6, Example 6

Lane 1=Pea extract at pH 8.0

Lane 2=Flow through fraction 1 (non-bound proteins) from load of adsorbent with the ligand DEAE Lane 3=Flow through fraction 2 (non-bound proteins) from load of adsorbent with the ligand DEAE Lane 4=Wash (non-bound and loosely bound proteins) of the adsorbent with the ligand DEAE Lane 5=Eluate (Bound and subsequently released proteins) from adsorbent with the ligand DEAE Lane 6=Flow through fraction 1 (non-bound proteins) from load of adsorbent with the ligand octylamine Lane 7=Flow through fraction 2 (non-bound proteins) from load of adsorbent with the ligand octylamine Lane 8=Wash (non-bound and loosely bound proteins) of the adsorbent with the ligand octylamine Lane 9=Eluate (Bound and subsequently released proteins) from adsorbent with the ligand octylamine Example 7

The example shows how specific pea proteins are captured from a pea extract where the main part of the pea proteins already have been removed by precipitation at pH 4.5 and decanting. An adsorbent coupled with the ligand SP (Produced as described in EXAMPLE 1), (the ligand concentration was determined with titration to be 129 mmol/L adsorbent) have been used to bind the proteins at pH 4.5.

The experiment was performed with Expanded Bed Adsorption (EBA) chromatography.

EBA column used for the experiment: 1 cm diameter laboratory EBA column with a 150 cm glass tube (Cat. No.: 7010-1500, Upfront Chromatography A/S, Denmark)

Procedure

The column was packed with 50 cm settled bed height, equal to 40 ml adsorbent. Flow rate during load of extract: 15 cm/min=12 ml/min. Flow rate during equilibration, wash and elution: 15 cm/min=12 ml/min. After packing the adsorbent was equilibrated with 200 ml 10 mM sodium citrate pH 4.5. The pea extract (produced at near neutral pH according to EXAMPLE 2) was pH-adjusted with 1 M HCl to pH 4.5, stirred for 1 hour, and the supernatant was decanted. The supernatant was loaded directly onto the column without centrifugation. 1200 ml of the extract was loaded onto the column. The flow through (non-bound proteins) was collected in four 300 ml fractions. The adsorbent was washed with 360 ml of deionized water. The flow through (non-bound and loosely bound proteins) was collected in one 330 ml fraction. The bound proteins were subsequently released from the column (eluted) by applying 275 ml of 30 mM NaOH. The eluate was collected in one fraction of 195 ml.

The performance of the adsorbent was determined by SDS-PAGE (as described in EXAMPLE 3). See FIG. 7. The SP ligand, see lane 8 representing the eluate fraction containing bound proteins, is binding the lipoxygenase at approx. 100 kDa and albumin at approx. 20-25 kDa. The flow through fractions are almost depleted from protein (see lanes 2, 3, 4, 5 and 6).

Dry matter determination was performed on the eluate (as described in EXAMPLE 3). The protein concentration in eluate was 10.9 mg/ml resulting in a yield of 1.8 mg protein per ml pea extract (supernatant) loaded onto the column. This results in a total adsorbent binding capacity of 54 mg protein per ml adsorbent.

Figure 7:
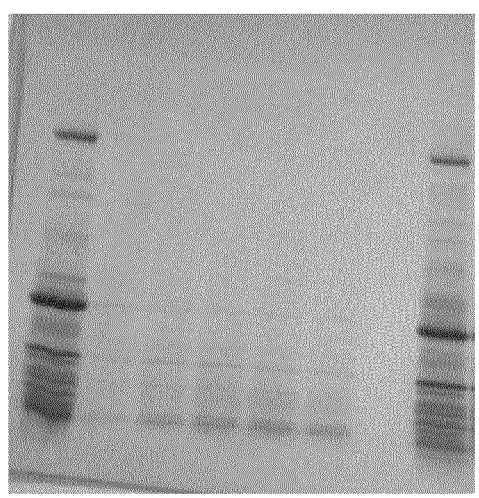

FIG. 7 in example 7

Lane 1=pea extract at pH 4.5 (supernatant)
Lane 2=Flow through fraction 1 (non-bound proteins) from load of adsorbent with the ligand SP at pH 4.5.
Lane 3=Flow through fraction 2 (non-bound proteins) from load of adsorbent with the ligand SP at pH 4.5.
Lane 4=Flow through fraction 3 (non-bound proteins) from load of adsorbent with the ligand SP at pH 4.5.
Lane 5=Flow through fraction 4 (non-bound proteins) from load of adsorbent with the ligand SP at pH 4.5.
Lane 6=Flow through pool of fraction 1 to 4 (non-bound proteins) from load of adsorbent with the ligand SP at pH 4.5.
Lane 7=Wash (non-bound and loosely bound proteins) of the adsorbent with the ligand SP.
Lane 8=Eluate (Bound and subsequently released proteins) from adsorbent with the ligand SP.

Example 8

The example shows how specific pea proteins are captured from a pea extract. The pea extract was produced by mixing 12.5 kg dried peas in 87.5 L deionised water for 60 minutes. The extract was hereafter left to sediment for 20 minutes and the supernatant was then decanted and used as load for the column. The pea proteins were bound using a benzylamine adsorbent at pH 6.3.

The experiment was performed with Expanded Bed Adsorption (EBA) chromatography.

EBA column used for the experiment: 30 cm diameter EBA column with a 150 cm glass tube (Cat. No.: 7300-1500, Upfront Chromatography A/S, Denmark)

Procedure

The column was packed with 50 cm settled bed height, equal to 35.3 L adsorbent. Flow rate during load of extract: 20 cm/min=14.1 L/min. Flow rate during equilibration, wash and elution: 20 cm/min=14.1 L/min. After packing the adsorbent was equilibrated with 150 L 10 mM potassium phosphate pH 6.3. The pea extract (produced at near neutral pH) was stirred for 1 hour, and the supernatant was decanted. The supernatant was loaded directly onto the column without centrifugation. 70.6 L of the extract was loaded onto the column. The flow through (non-bound proteins) was collected in one fraction but samples were taken for every 17.5 L. The adsorbent was washed with 250 L of deionized water. The bound proteins were subsequently released from the column (eluted) by applying 70 L of 30 mM NaOH. The eluate was collected in one fraction of 70 L which was continuously pH adjusted during collection to pH 7 to 9. The total eluate had after collection a pH of 7.5 and a conductivity of 1975 µS/cm.

The performance of the adsorbent was determined by SDS-PAGE (as described in EXAMPLE 3). See FIG. 8. The benzylamine ligand, see lane 6 representing the eluate fraction containing bound proteins, binds the lipoxygenase at approx. 100 kDa, Convicilin at at 70 kDa, and vicilin at approx. 45 kDA and albumin at 20-25 kDa. The flow-through fractions contain legumin at 60 kDa and vicilin (see lanes 2, 3, 4 and 5).

Dry matter determination was performed on the eluate (as described in EXAMPLE 3). The protein concentration in eluate was 13.5 mg/ml resulting in a yield of 13.5 mg protein per ml pea extract (supernatant) loaded onto the column. This results in a total adsorbent binding capacity of 26.8 mg protein per ml adsorbent.

Figure 8:
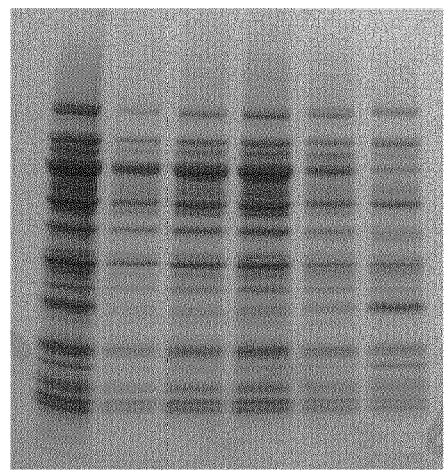

FIG. 8 in example 8

Lane 1=pea extract at near neutral pH (supernatant)
Lane 2=Flow through sample 1 (non-bound proteins) from load of adsorbent with the ligand benzylamine at pH 6.3.
Lane 3=Flow through sample 2 (non-bound proteins) from load of adsorbent with the ligand benzylamine at pH 6.3.
Lane 4=Flow through sample 3 (non-bound proteins) from load of adsorbent with the ligand benzylamine at pH 6.3.
Lane 5=Flow through sample 4 (non-bound proteins) from load of adsorbent with the ligand benzylamine at pH 6.3.
Lane 6=Eluate (Bound and subsequently released proteins) from adsorbent with the ligand benzylamine.

Example 9

The example shows how specific pea proteins are captured from a pea extract. The pea extract was produced by mixing 12.5 kg dried peas in 87.5 L deionised water for 60 minutes. The extract was hereafter adjusted to pH 8.0 and left to sediment for 20 minutes. The supernatant was then decanted and used as load for the column. The pea proteins were bound using a benzylamine adsorbent at pH 8.0.

The experiment was performed with Expanded Bed Adsorption (EBA) chromatography.

EBA column used for the experiment: 30 cm diameter EBA column with a 150 cm glass tube (Cat. No.: 7300-1500, Upfront Chromatography A/S, Denmark)

Procedure

The column was packed with 50 cm settled bed height, equal to 35.3 L adsorbent. Flow rate during load of extract: 20 cm/min=14.1 L/min. Flow rate during equilibration, wash and elution: 20 cm/min=14.1 L/min. After packing the adsorbent was equilibrated with 300 L 10 mM potassium phosphate pH 8.0. The supernatant from the pea extract was loaded directly onto the column without centrifugation. 60 L of the supernatant was loaded onto the column. The flow through (non-bound proteins) was collected in one fraction but samples were taken for every 20 L. The adsorbent was washed with 250 L of deionized water. The bound proteins were subsequently released from the column (eluted) by applying 80 L of 30 mM NaOH. The eluate was collected in one fraction of 70 L which was continuously pH adjusted during collection to pH 7 to 9. The total eluate had after collection a pH of 7.3 and a conductivity of 2.38 mS/cm.

The performance of the adsorbent was determined by SDS-PAGE (as described in EXAMPLE 3). See FIG. 9. The benzylamine ligand, see lane 5 representing the eluate fraction containing bound proteins, is binding the lipoxygenase at approx. 100 kDa, Convicilin at at 70 kDa, and vicilin at approx. 45 kDA and some of the albumin at 20 kDa. The flow through fractions contains legumin at 60 kDa and vicilin (see lanes 2, 3 and 4).

Dry matter determination was performed on the eluate (as described in EXAMPLE 3). The protein concentration in eluate was 4.8 mg/ml resulting in a yield of 5.6 mg protein per ml pea extract (supernatant) loaded onto the column. This results in a total adsorbent binding capacity of 9.6 mg protein per ml adsorbent.

Figure 9:
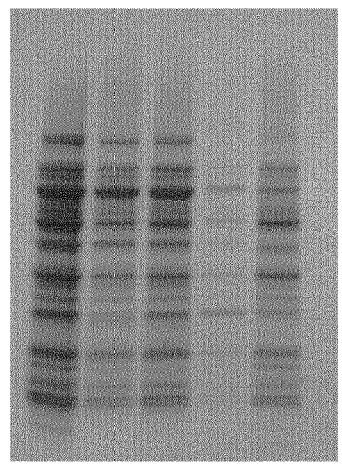

FIG. 9 in example 9
Lane 1=pea extract at pH 8.0 (supernatant)
Lane 2=Flow through sample 1 (non-bound proteins) from load of adsorbent with the ligand benzylamine at pH 8.0.
Lane 3=Flow through sample 2 (non-bound proteins) from load of adsorbent with the ligand benzylamine at pH 8.0.
Lane 4=Flow through sample 3 (non-bound proteins) from load of adsorbent with the ligand benzylamine at pH 8.0.
Lane 5=Eluate (Bound and subsequently released proteins) from adsorbent with the ligand benzylamine.

Example 10

The example shows how specific pea proteins are captured from a pea extract. The pea extract was produced as described in example 9 but during the extraction 0.5 mg/ml sodium sulphite was added to the mix. Hence 12.5 kg dried peas and 50 g of sodium sulphite was mixed in 87.5 L deionised water for 60 minutes. The extract was hereafter adjusted to pH 8.0 and left to sediment for 20 minutes. The supernatant was then decanted and used as load for the column. The pea proteins were bound using a benzylamine adsorbent at pH 8.0.

The experiment was performed with Expanded Bed Adsorption (EBA) chromatography.

EBA column used for the experiment: 30 cm diameter EBA column with a 150 cm glass tube (Cat. No.: 7300-1500, Upfront Chromatography A/S, Denmark)

Procedure

The column was packed with 50 cm settled bed height, equal to 35.3 L adsorbent. Flow rate during load of extract: 20 cm/min=14.1 L/min. Flow rate during equilibration, wash and elution: 20 cm/min=14.1 L/min. After packing the adsorbent was equilibrated with 300 L 10 mM potassium phosphate pH 8.0. The supernatant from the pea extract was loaded directly onto the column without centrifugation. 60 L of the supernatant was loaded onto the column. The flow through (non-bound proteins) was collected in one fraction but samples were taken for every 20 L. The adsorbent was washed with 300 L of deionized water. The bound proteins were subsequently released from the column (eluted) by applying 80 L of 30 mM NaOH. The eluate was collected in one fraction of 60 L which was continuously pH adjusted during collection to pH 7 to 9. The total eluate had after collection a pH of 7.0 and a conductivity of 1.96 mS/cm.

The performance of the adsorbent was determined by SDS-PAGE (as described in EXAMPLE 3). See FIG. 10. The benzylamine ligand, see lane 7 representing the eluate fraction containing bound proteins, is binding the lipoxygenase at approx. 100 kDa, Convicilin at at 70 kDa, and vicilin at approx. 45 kDA and albumin at 20 kDa. The flow through fractions contains legumin at 60 kDa and vicilin (see lanes 2, 3 and 4).

Dry matter determination was performed on the eluate (as described in EXAMPLE 3). The protein concentration in eluate was 5.5 mg/ml resulting in a yield of 5.5 mg protein per ml pea extract (supernatant) loaded onto the column. This results in a total adsorbent binding capacity of 9.3 mg protein per ml adsorbent.

Figure 10:
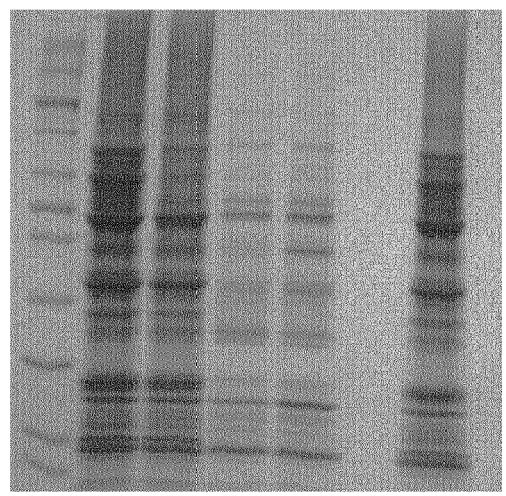

FIG. 10 in example 10
Lane 1=Standard marker as described in example 3.
Lane 2=pea extract containing sulphite at pH 8.0 (supernatant)
Lane 3=Flow through sample 1 (non-bound proteins) from load of adsorbent with the ligand benzylamine at pH 8.0.
Lane 4=Flow through sample 2 (non-bound proteins) from load of adsorbent with the ligand benzylamine at pH 8.0.
Lane 5=Flow through sample 3 (non-bound proteins) from load of adsorbent with the ligand benzylamine at pH 8.0.
Lane 6=Blank
Lane 7=Eluate (Bound and subsequently released proteins) from adsorbent with the ligand benzylamine.

Example 11

The example shows how specific pea proteins are captured from a pea extract where the main part of the pea proteins already have been precipitated at pH 4.5 and decanted using an adsorbent coupled with the ligand SP (Produced as described in EXAMPLE 1), (the ligand concentration was determined with titration to be 129 mmol/L adsorbent), where the proteins have been bound at pH 4.5.

The experiment was performed with Expanded Bed Adsorption (EBA) chromatography.

EBA column used for the experiment: 30 cm diameter laboratory EBA column with a 150 cm glass tube (Cat. No.: 7300-1500, Upfront Chromatography A/S, Denmark)

Procedure

The column was packed with 44 cm settled bed height, equal to 31.1 L adsorbent. Flow rate during load of extract: 15 cm/min=10.6 L/min. Flow rate during equilibration, wash and elution: 15 cm/min=10.6 L/min. After packing the adsorbent was equilibrated with 200 L 10 mM sodium citrate pH 4.5. The pea extract (produced at near neutral pH according to EXAMPLE 2) was pH-adjusted with 1 M HCl to pH 4.5, stirred for 1 hour, and the supernatant was decanted. The supernatant was loaded directly onto the column without centrifugation. 62 L of the extract was loaded onto the column. The flow through (non-bound proteins) was collected in one fraction but samples were taken for every 30 L. The adsorbent was washed with 300 L of deionized water. The bound proteins were subsequently released from the column (eluted) by applying 70 L of 30 mM NaOH. The eluate was collected in one fraction of 52.3 L which was continuously pH adjusted during collection to pH 7 to 9. The total eluate had after collection a pH of 7.2 and a conductivity of 1.54 mS/cm.

The performance of the adsorbent was determined by SDS-PAGE (as described in EXAMPLE 3). See FIG. 11. The SP ligand, see lane 5 representing the eluate fraction containing bound proteins, is binding all protein available in the supernatant. The flow-through fractions are almost depleted from protein (see lanes 3 and 4).

Dry matter determination was performed on the eluate (as described in EXAMPLE 3). The protein concentration in eluate was 12.8 mg/ml resulting in a yield of 10.8 mg protein per ml pea extract (supernatant) loaded onto the column. This results in a total adsorbent binding capacity of 21.5 mg protein per ml adsorbent.

Figure 11:
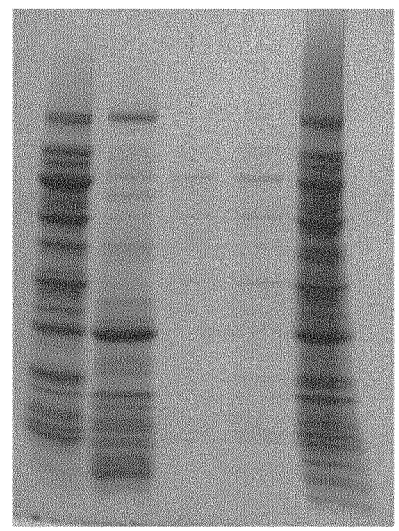

FIG. 11 in example 11
Lane 1=pea extract before pH adjustment (supernatant)
Lane 2=pea extract at pH 4.5 (supernatant)
Lane 3=Flow through fraction 1 (non-bound proteins) from load of adsorbent with the ligand SP at pH 4.5.
Lane 4=Flow through fraction 2 (non-bound proteins) from load of adsorbent with the ligand SP at pH 4.5.
Lane 5=Eluate (Bound and subsequently released proteins) from adsorbent with the ligand SP.

Example 12

The example illustrates selected functional properties of different pea protein fractions produced as described in examples 8, 9, 10 and 11.

Four pea protein fractions and a commercial pea protein were tested for the selected functional properties:

Pea Protein Fractions
1. Commercial pea protein: Pea protein MEGA (Cat. No.: 480 from Natur Drogeriet A/S, Denmark)
2. Pea protein fraction 1, PPF1 (described in example 8)
3. Pea protein fraction 2, PPF2 (described in example 9)
4. Pea protein fraction 3, PPF3 (described in example 10)
5. Pea protein fraction 4, PPF4 (described in example 11)

Figure 12:
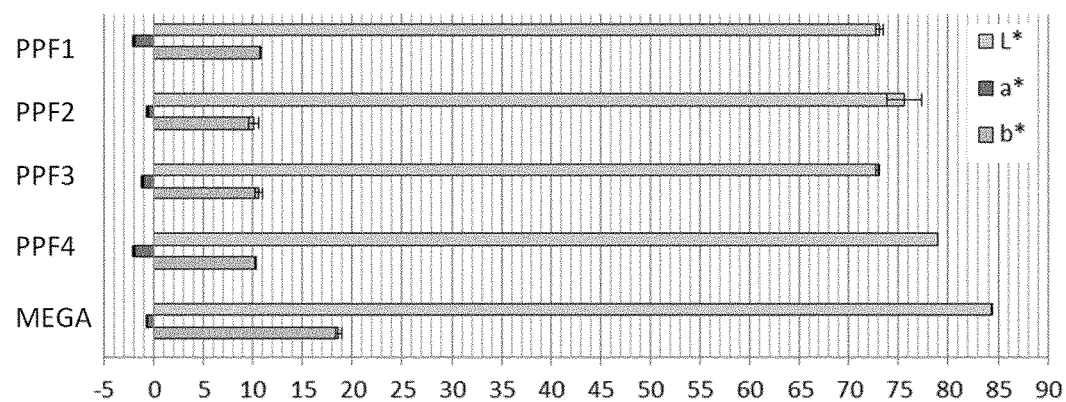

Selected Functional Properties Tested
1. Color (using the CIE Lab color measurement)
2. pH of pea protein fraction
3. Foaming capacity and stability
4. Gelling strength and temperature
5. Emulsion capacity and stability Color The color of the pea protein fractions have been measured using the CIE Lab color measurement method. FIG. 12 shows the results from this measurement for each of the pea protein fractions. All the tested pea proteins are white to light yellow however the pea protein fractions 1 to 4 are less yellow compared to the commercial pea protein (MEGA) which is observed by the lower b* value in the FIG. 12.

pH of Pea Protein Fraction

Figure 13:
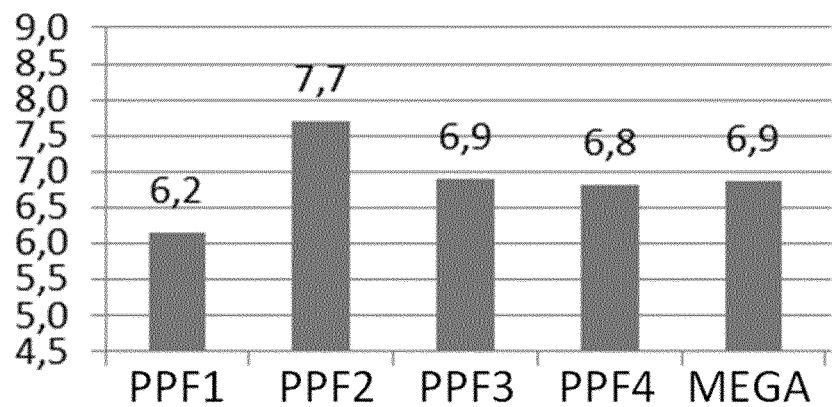

FIG. 13 shows the measured pH values for 3% solutions of the pea protein fractions. All the tested pea proteins have a starting pH at neutral pH. Pea protein fraction 2 has a slightly higher pH value compared to the commercial pea protein, MEGA.

Foaming Capacity and Stability

Figure 14A:
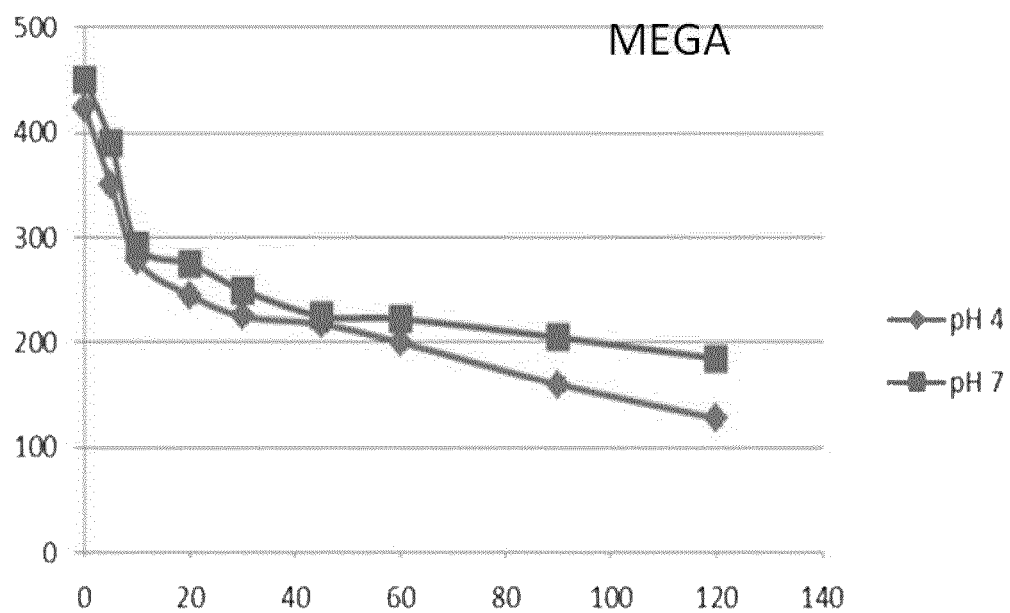
Figure 14B:
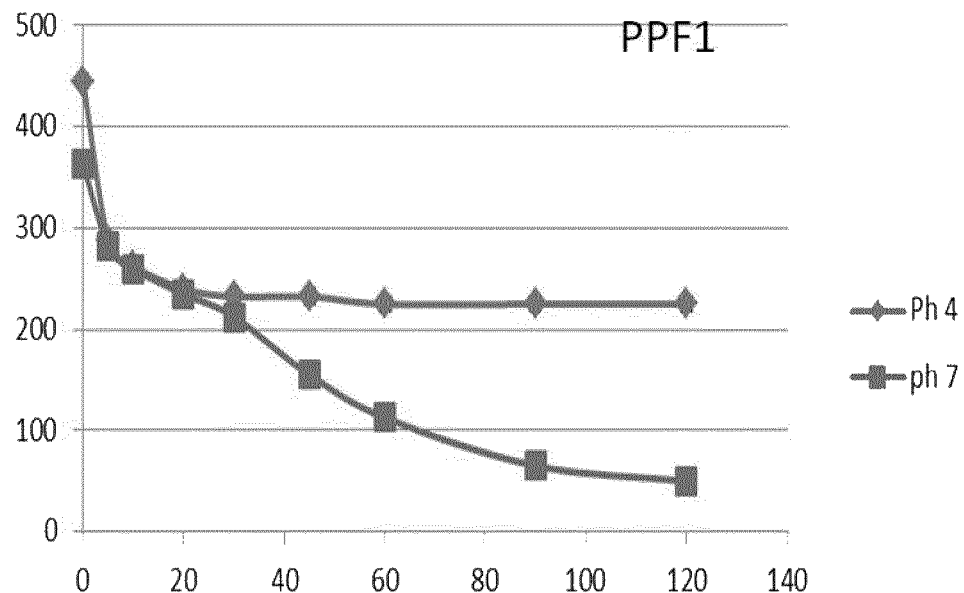
Figure 14C:
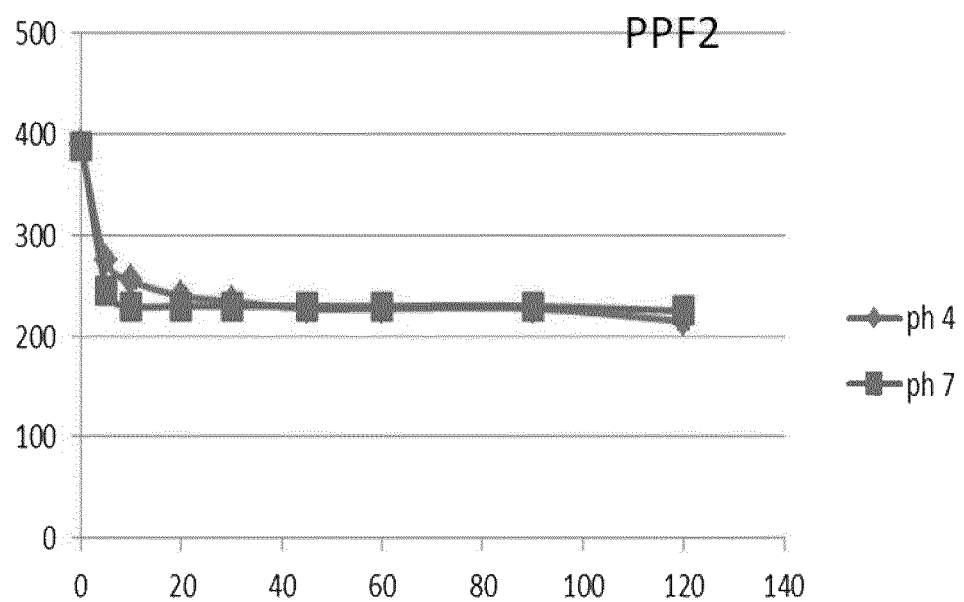
Figure 14D:
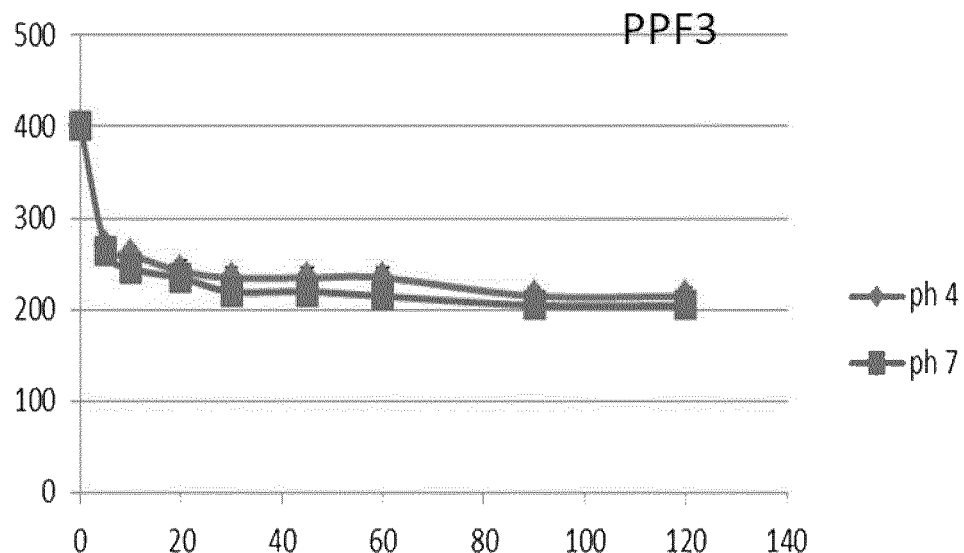
Figure 14E:
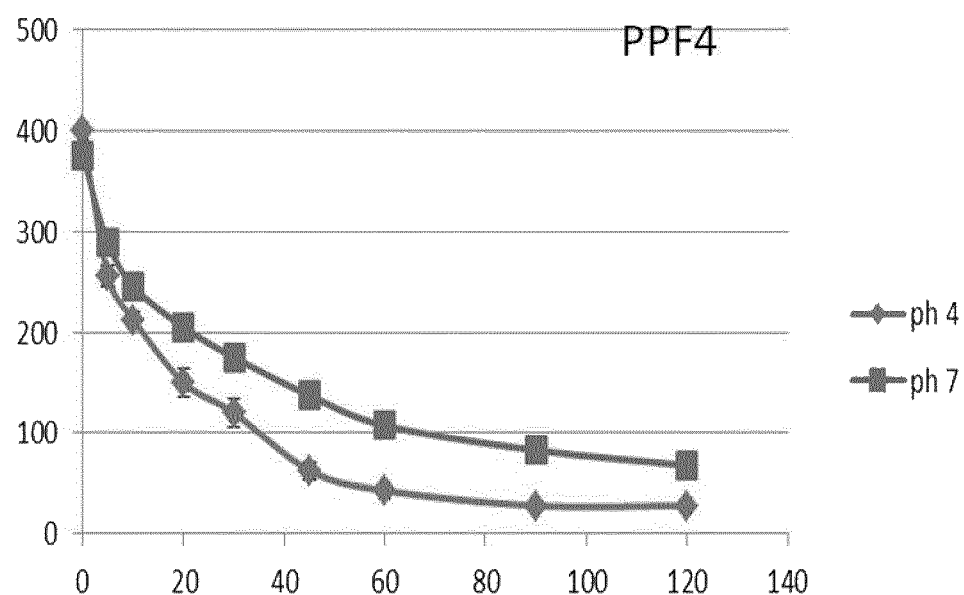
Figure 14F:
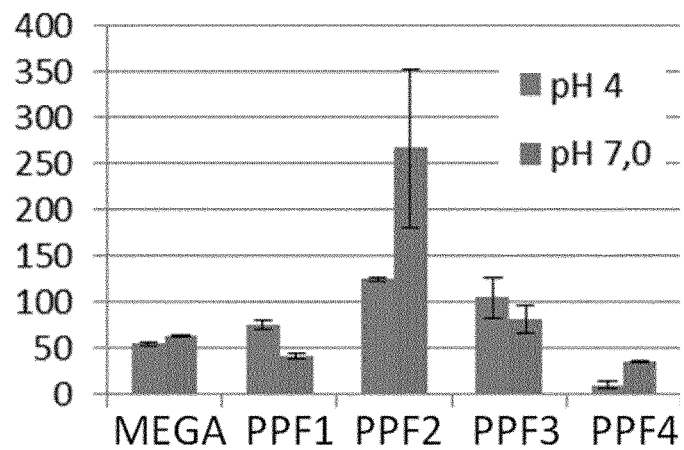

The foaming capacity and stability of the pea protein fractions (PPF1-PPF4 and MEGA) have been measured by dissolving 3% pea protein in deionized water, adjusting pH to 7.0 and mixing the pea protein solution for 5 min at 20.000 rpm using an Ultra Turrex. The foaming capacity is measured as the volume increase in percentage and the foaming stability as the time for the foam to reduce itself to 50% of the foaming capacity. FIGS. 14a-14f show the measured values. From FIGS. 14b, 14c and 14d, it is observed that pea protein fraction 1 at pH 4, fraction 2 and fraction 3 have equal or higher foaming capacity over time than the commercial pea protein (FIG. 14a). In FIG. 14f the pea protein fraction 2 shows excellent foaming stability at both pH 4 and especially pH 7.

FIG. 14a-14e in example 12, foaming capacity (Y-axis: volume increase in %, X-axis: time in minutes)

FIG. 14f in example 12, foaming stability (Y-axis: volume increase in %)

Gelling Strength and Temperature

Figure 15A:
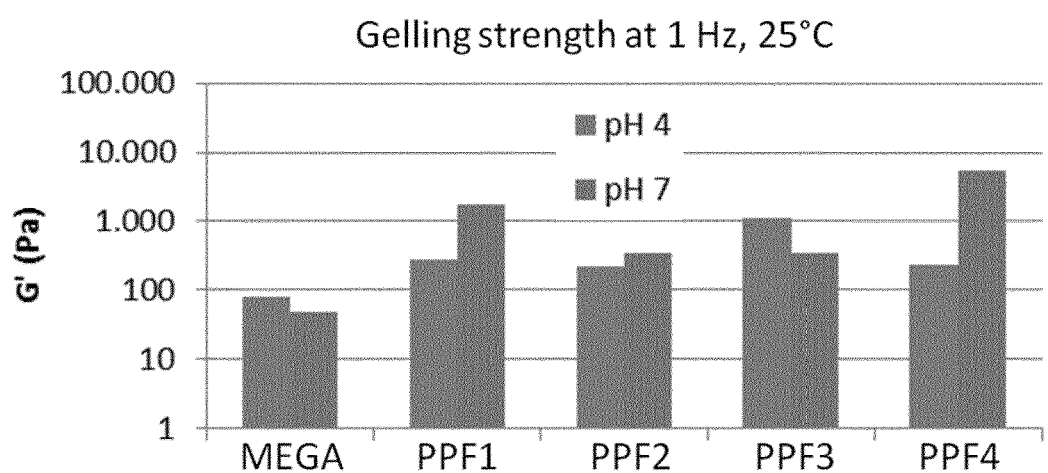
Figure 15B:
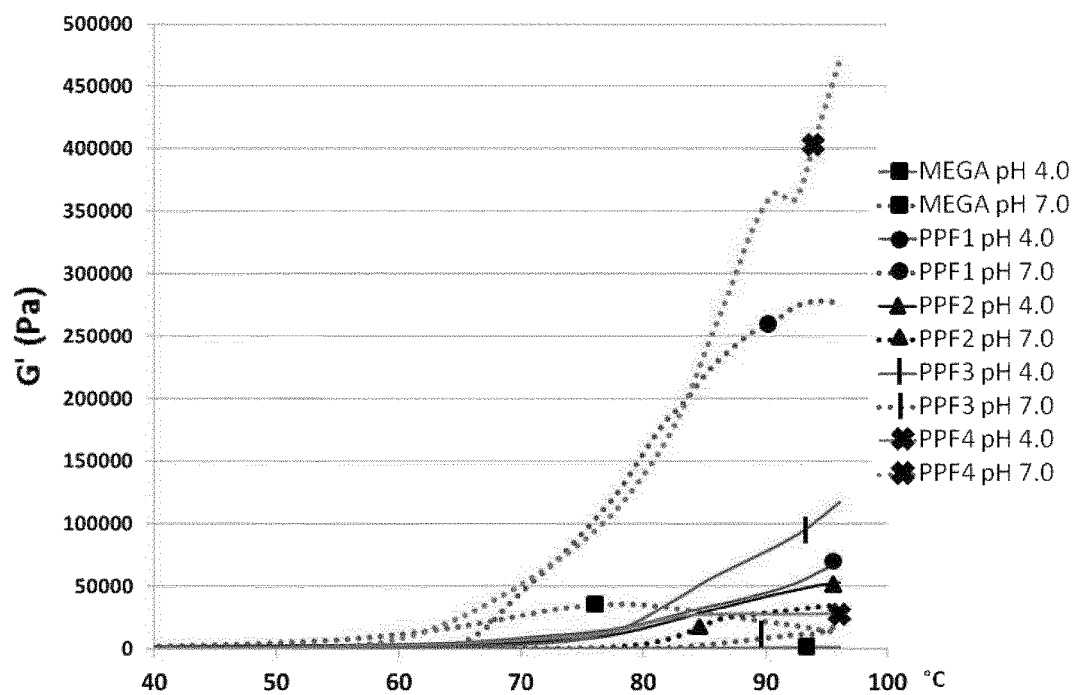

The gelling strength of the pea protein fractions have been measured by dissolving 12.5% pea protein in deionized water. The pea protein solution is heated 2° C. per minute from 25° C. to 90° C. while measuring the elasticity and viscosity of the gel using a rheometer physica MCR301 from Anton Paar. The gel is hereafter cooled to 25° C. in the rheometer and the gelling strength is measured at 1 Hz. FIG. 15a shows the measured gelling strengths and FIG. 15b shows the measured values for the gelling strength versus temperature from 40° C. to 95° C. FIG. 15a indicates that all the pea protein fractions have equal or higher gelling strength than the commercial pea protein, MEGA. In FIG. 15b it is observed that especially pea protein fraction 1 and 4 at pH 7 have superior gelling strength at elevated temperatures.

FIG. 15b in example 12 (Y-axis: gelling strength (G') in Pa, X-axis: temperature in celsius)

Emulsion Capacity and Stability

The emulsion capacity and stability of the pea protein fractions have been measured by dissolving 1% pea protein in deionized water. The pea protein solution is then mixed with rapeseed oil in the ratio 1:1. The mix is then stirred using a Ultra Thurrax at 20.000 rpm until an emulsion is observed. Hereafter the emulsion (the whole sample) is centrifuged at 1500×g for 5 minutes. The emulsion capacity is then calculated as the percentage of emulsion volume per total volume of the sample. The calculated values are shown in FIG. 16a.

The emulsion stability is then obtained by heating the sample (emulsion) to 80° C. for 30 minutes and is left for 15 minutes of cooling at room temperature. Hereafter is the sample centrifuged at 1500×g for 5 minutes. The emulsion stability is then calculated as the percentage of emulsion volume per total volume of the sample. The calculated values are shown in FIG. 16b.

Figure 16A:
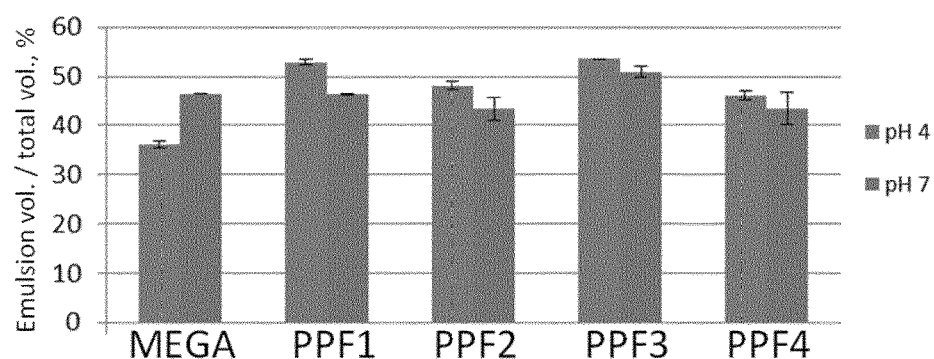
Figure 16B:
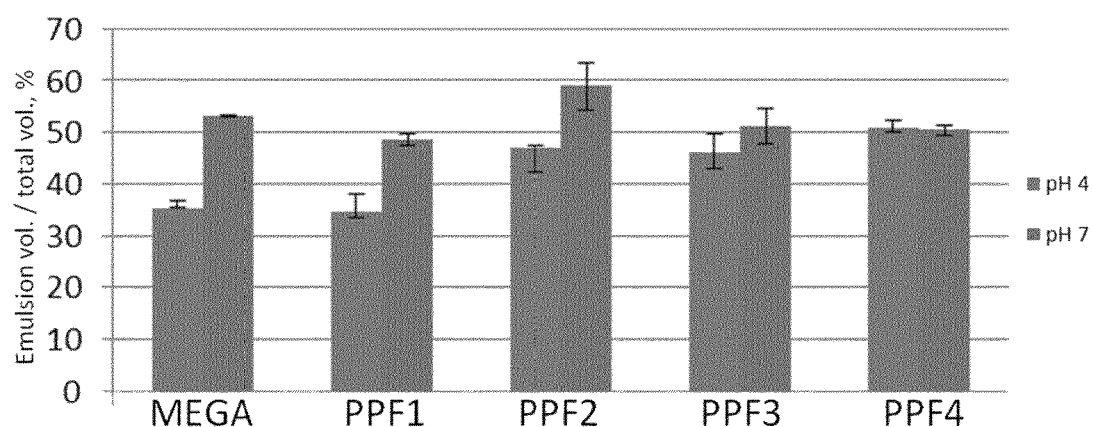

FIGS. 16a and 16b show that the tested pea protein fraction 1 to 4 all have equal or higher emulsion capacity and stability compared to the commercial pea protein, MEGA.

The invention claimed is:

1. A process for the separation of pea protein, said process comprising the steps of:
   i. providing an aqueous extract of pea protein or a solution of pea protein, said extract or solution of pea protein comprising at least two types of pea proteins;
   ii. passing said aqueous extract or solution of pea protein through at least one expanded bed absorption process, wherein said expanded bed absorption process comprises contacting said aqueous extract or solution of pea protein with at least one adsorbent resin which selectively adsorbs at least a first type of pea protein to provide a non-bound protein fraction and a bound protein fraction, said adsorbent resin comprising:

at least one ligand (L1), said at least one ligand (L1) comprising an aromatic or heteroaromatic ring system and one or more acidic groups, or at least one ligand (L2), said at least one ligand (L2) comprising an alkylamine or alkylarylamine, wherein said alkylamine or alkylarylamine moieties in ligands (L2) comprise an amine substituted with one or more groups selected from:
  a. an aryl, benzyl or heteroaryl group;
  b. an alkyl group having 4-16 carbon atoms which may be straight, branched or cyclic;
  or combinations thereof;

iii. isolating said first type of pea protein from said adsorbent resin, by elution of either the non-bound protein fraction or of the bound protein fraction; and iv. isolating the second type of pea protein from said adsorbent resin to provide a second pea protein composition which is depleted in said first type of pea protein.

2. The process according to claim 1, further comprising the step of denaturing the second pea protein composition to provide a denatured second pea protein composition.

3. The process according to any one of the preceding claims, wherein the ligands (L1) comprise an aromatic ring system.

4. The process according to claim 1, wherein said alkylamine or alkylarylamine moieties in ligands (L2) comprise an amine substituted with one or more groups selected from: an alkyl group having 4-16 carbon atoms which may be straight, branched or cyclic.

5. The process according to claim 1, wherein said ligands (L2) are selected from butylamine, hexylamine, octylamine di-butylamine, pentylamine, n-pentylamine, N,N-di-methyl-1,3-di-aminopropane, 1,3-diaminopropane, 1,6-diamino hexane, 1,6-diamino hexane, 1,8-aminooctane, 1,9-di-aminononane, 1,12-aminododecane, 2-aminobenzylamine, 2-aminobenzimidazole, 2-aminoimidazole, 2,4-di-amino-6-hydroxypyrimidine or benzylamine.

6. The process according to claim 1, wherein the ligands (L1) comprise a phenyl or naphthyl radical.

7. The process according to claim 1, wherein said alkylamine or alkylarylamine moieties in ligands (L2) comprise an amine substituted with one or more groups selected from: butyl, isobutyl, tert-butyl, pentyl, hexyl, heptyl, octyl, nonyl, decyl, undecyl, dodecyl, cyclopentyl, cyclohexyl or decalinyl.

* * * * *